US012603182B2

(12) United States Patent (10) Patent No.: US 12,603,182 B2
Röder et al. (45) Date of Patent: Apr. 14, 2026

(54) INTERPRETATION OF MACHINE LEARNING CLASSIFICATIONS IN CLINICAL DIAGNOSTICS USING SHAPLEY VALUES AND USES THEREOF

(71) Applicant: BIODESIX, INC., Boulder, CO (US)

(72) Inventors: Heinrich Röder, Steamboat Springs, CO (US); Joanna Röder, Steamboat Springs, CO (US); Laura Maguire, Boulder, CO (US); Robert W. Georgantas, III, Broomfield, CO (US); Thomas Campbell, Thronton, CO (US); Lelia Net, Boulder, CO (US)

(73) Assignee: Biodesix, Inc., Louisville, CO (US)

( * ) Notice: Subject to any disclaimer, the term of this patent is extended or adjusted under 35 U.S.C. 154(b) by 977 days.

(21) Appl. No.: 17/360,254

(22) Filed: Jun. 28, 2021

(65) Prior Publication Data

US 2022/0188701 A1 Jun. 16, 2022

Related U.S. Application Data

(60) Provisional application No. 63/125,527, filed on Dec. 15, 2020.

(51) Int. Cl.
*G16H 50/30* (2018.01)
*G06N 20/00* (2019.01)
(Continued)

(52) U.S. Cl.
CPC ............. *G16H 50/30* (2018.01); *G06N 20/00* (2019.01); *G16H 10/60* (2018.01); *G16H 15/00* (2018.01); *G16H 40/20* (2018.01); *G16H 50/20* (2018.01)

(58) Field of Classification Search
CPC .. G06F 18/213; G06F 18/2163; G06F 18/251; G06F 18/2415; G06N 3/048;
(Continued)

(56) References Cited

U.S. PATENT DOCUMENTS 7,572,596 B2 * 8/2009 Bowser ................ A61K 38/095
435/7.1
7,736,905 B2 6/2010 Roder et al.
(Continued)

OTHER PUBLICATIONS

Adam J. Singer, MD et al., "Point-of-care testing reduces length of stay in emergency department chest pain patients", Jun. 2005 vol. 45 No. 6 (Year: 2005).*

(Continued)

*Primary Examiner* — Miranda M Huang
(74) *Attorney, Agent, or Firm* — Lathrop GPM LLP; Lisa Hillman

(57) ABSTRACT

Shapley values (SVs) have become an important tool to further the goal of explainability of machine learning (ML) models. However, the computational load of exact SV calculations increases exponentially with the number of attributes. Hence, the calculation of SVs for models incorporating large numbers of interpretable attributes is problematic. Molecular diagnostic tests typically seek to leverage information from hundreds or thousands of attributes, often using training sets with fewer instances. Methods are described for evaluate SVs using Monte Carlo sampling or exact calculation in polynomial time (i.e., reasonably quickly and efficiently) using the architecture of a ML model designed for robust molecular test generation, and without requiring classifier retraining.

13 Claims, 28 Drawing Sheets

(51) Int. Cl.

| | |
|---|---|
| *G16H 10/60* | (2018.01) |
| *G16H 15/00* | (2018.01) |
| *G16H 40/20* | (2018.01) |
| *G16H 50/20* | (2018.01) |

(58) Field of Classification Search

CPC .......... G06N 3/08; G06N 3/044; G06N 3/045;
G06N 3/049; G06N 20/00; G06N 7/01;
G06N 5/01; Y02D 10/00; G06V 10/82;
G06V 10/7715; G06V 10/40; G16H
50/30; G16H 10/60; G16H 15/00; G16H
40/20; G16H 50/20; G16H 50/70

See application file for complete search history.

(56) References Cited

U.S. PATENT DOCUMENTS

| | | | | |
|---|---|---|---|---|
| 8,433,669 | B2 | 4/2013 | Amini et al. | |
| 10,007,766 | B2 | 6/2018 | Röder et al. | |
| 10,037,874 | B2 | 7/2018 | Röder et al. | |
| 10,594,529 | B1 | 3/2020 | Delmarco | |
| 10,950,348 | B2 | 3/2021 | Röder et al. | |
| 11,476,003 | B2 | 10/2022 | Campbell et al. | |
| 11,710,564 | B1 * | 7/2023 | Maier | G16H 10/20 706/11 |
| 11,894,147 | B2 | 2/2024 | Campbell et al. | |
| 11,977,991 | B1 * | 5/2024 | Mugan | G06N 5/045 |
| 2010/0293207 | A1 | 11/2010 | Parthasarathy et al. | |
| 2011/0295622 | A1 | 12/2011 | Farooq et al. | |
| 2012/0197896 | A1 | 8/2012 | Li et al. | |
| 2013/0288244 | A1 * | 10/2013 | Deciu | C12Q 1/6827 702/20 |
| 2013/0338933 | A1 * | 12/2013 | Deciu | C12Q 1/6827 702/20 |
| 2014/0093873 | A1 * | 4/2014 | Tynan | C12Q 1/6881 435/6.11 |
| 2015/0050308 | A1 | 2/2015 | Hook | |
| 2015/0102216 | A1 | 4/2015 | Roder et al. | |
| 2020/0211716 | A1 * | 7/2020 | Lefkofsky | G06F 18/214 |
| 2020/0400668 | A1 | 12/2020 | Eden et al. | |
| 2021/0118538 | A1 | 4/2021 | Oliveira et al. | |
| 2021/0147448 | A1 * | 5/2021 | Kanai | A61P 1/02 |
| 2022/0059242 | A1 | 2/2022 | Schneider et al. | |
| 2022/0189638 | A1 | 6/2022 | Campbell et al. | |
| 2023/0005621 | A1 | 1/2023 | Campbell et al. | |
| 2023/0290452 | A1 | 9/2023 | Kast et al. | |

OTHER PUBLICATIONS

H Robert Bergen III, et al., "identification of Transthyretin variations by sequential proteomic and Genomic Analysis", 2004 (Year: 2004).*

Robert Bergen et al ; "Identification of Transthyretin Variants by Sequential Proteomic and Genomic Analysis"; Clinical Chemistry 1544-1552 (2004) (Year: 2004).*

Adam Singer et al ; "Point-of-Care Testing Reduces Length of Stay in Emergency Department Chest Pain Patients" ; Copyright ᵃ 2005 by the American College of Emergency Physicians. doi: 10.1016/j.annemergmed.2004.11.020 (Year: 2005).*

Random Forest "Radom Forest", Oct. 2025, p. 12, https://en.wikipedia.org/wiki/Random_forest.*

Aas et al., "Explaining Individual Predictions When Features Are Dependent: More Accurate Approximations to Shapley Values", 26 pages, Mar. 25, 2019.

Asceierto et al., "Proteomic test for anti-PD-1 checkpoint blockade treatment of metastatic melanoma with and without BRAF mutations", Journal for ImmunoTherapy of Cancer, vol. 7, No. 91, 8 pages, (2019).

Jia et al, "Towards Efficient Data Valuation Based on the Shapley Value", Proceedings of the 22nd International Conference on Artificial Intelligence and Statistics (AIS-TATS) PMLR, vol. 89, 10 pages, (2019).

Kasimir-Bauer et al, "Definition and Independent Validation of a Proteomic-Classifier in Ovarian Cancer", Cancers, vol. 12, No. 2519, 17 pages, Sep. 4, 2020.

Lundberg et al., "A Unified Approach to Interpreting Model Predictions", 31st Conference on Neural Information Processing Systems (NIPS 2017), 10 pages, (2017).

Merrick et al, "The Explanation Game: Explaining Machine Learning Models Using Shapley Values", 20 pages, Aug. 18, 2020.

Molnar, "Interpretable Machine Learning, A Guide for Making Black Box Models Explainable", Chapter 5.9, Nov. 20, 2020.

Ribeiro et al, "'Why Should I Trust You?' Explaining the Predictions of Any Classifier", Proceedings of the 22nd ACM SIGKDD International Conference on Knowledge Discovery and Data Mining, pp. 1135-1144, Aug. 13, 2016.

Röder et al., "A drop out-regularized classifier development approach optimized for precision medicine test discovery from omics data", BMC Bioinformatics, vol. 20, No. 325, 14 pages, Jun. 13, 2019.

Röder et al., "Robust identification of molecular phenotypes using semi-supervised learning", BMC Informatics, vol. 20, No. 273, 25 pages, May 28, 2019.

Shapley, "A value for n-person games", The Shapley Value, Chapter 2, pp. 31-40, (1988).

Štrumbelj et al., "An Efficient Explanation of Individual Classifications of Game Theory", Journal of Machine Learning Research, vol. 11, pp. 1-18, (2010).

Štrumbelj et al., "Explaining prediction models and individual predictions with feature contributions", Knowledge and Information Systems, vol. 41, pp. 647-665, Aug. 30, 2013.

Williamson et al., "Efficient nonparametric statistical inference on population feature importance using Shapley values", Proceedings of the 37th International Conference on Machine Learning PMLR, vol. 119, (2020).

International Search Report and Written Opinion issued in PCT/US2021/063560 dated Jan. 19, 2022 (10 pages).

* cited by examiner

50 — OBTAIN SET OF FEATURE VALUES

52 — CLASSIFY WITH TRAINED ML CLASSIFIER TO GENERATE PREDICTION

54 — CALCULATE RELATIVE CONTRIBUTION OF FEATURES TO THE PREDICTION (SVs)

56 — GENERATE REPORT
1. PREDICTION
2. SVs
3. COMMENTS (OPTIONAL)

FIG. 3C

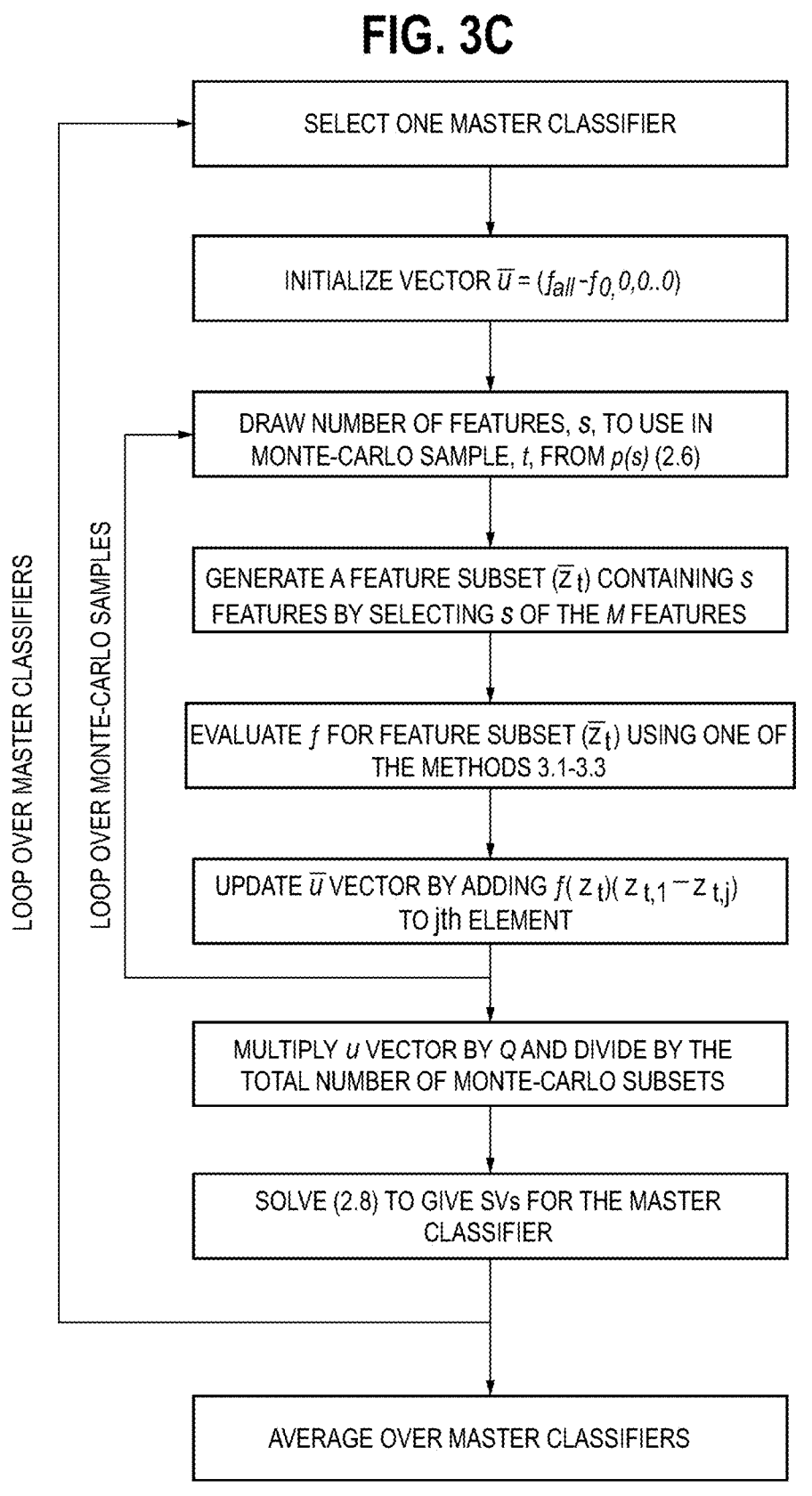

SELECT ONE MASTER CLASSIFIER

INITIALIZE VECTOR $\bar{u} = (f_{all} - f_0, 0, 0..0)$

DRAW NUMBER OF FEATURES, $s$, TO USE IN MONTE-CARLO SAMPLE, $t$, FROM $p(s)$ (2.6)

GENERATE A FEATURE SUBSET $(\bar{z}_t)$ CONTAINING $s$ FEATURES BY SELECTING $s$ OF THE $M$ FEATURES EVALUATE $f$ FOR FEATURE SUBSET $(\bar{z}_t)$ USING ONE OF THE METHODS 3.1-3.3

UPDATE $\bar{u}$ VECTOR BY ADDING $f(z_t)(z_{t,1} - z_{t,j})$ TO jth ELEMENT

MULTIPLY $u$ VECTOR BY $Q$ AND DIVIDE BY THE TOTAL NUMBER OF MONTE-CARLO SUBSETS

SOLVE (2.8) TO GIVE SVs FOR THE MASTER CLASSIFIER

AVERAGE OVER MASTER CLASSIFIERS

LOOP OVER MASTER CLASSIFIERS

LOOP OVER MONTE-CARLO SAMPLES

INTERPRETATION OF MACHINE LEARNING CLASSIFICATIONS IN CLINICAL DIAGNOSTICS USING SHAPLEY VALUES AND USES THEREOF

PRIORITY

This application claims priority benefits of U.S. Provisional Application 63/125,527 filed on Dec. 15, 2020. The entire content of the '527 application, including Appendices A, B and C thereof, is incorporated by reference herein.

BACKGROUND

Advancements in machine learning, and the applications of machine learning (ML), to the health and diagnostics fields, have led to the development of tests which can predict response to specific treatments in advance, or assess risk for unfavorable outcomes in hospitalized patients. Such tests use trained ML models or trained classifiers. For example, the Assignee of this invention has developed tests for predicting patient response to certain types of treatments in cancer, and risk of recurrence of cancer, using mass spectrometry data obtained from blood-based samples. See, for example, the following patents: U.S. Pat. Nos. 7,736,905; 10,950,348; 10,594,529; 10,007,766; and 10,037,874 and U.S. Patent Application publication no. 2021/0118538.

Our prior U.S. provisional application Ser. No. 63/125,527 filed on Dec. 15, 2020 describes a test for predicting risk of certain clinical outcomes for patients hospitalized with infection of the SARS-Cov-2 virus from basic patient characteristics, laboratory data and clinical data including findings at admission to the hospital. The risk assessment tests described in that application are good examples of how machine learning can be used to combine many patient attributes to produce a test able to predict a future clinical outcome with sufficient accuracy to provide clinical utility to physicians and patients. While the predictive accuracy of tests developed with modern ML can be high, the approach lacks transparency into the biological or clinical rationale underlying the test and does not provide a simple explanation of how the result for an individual patient is obtained from the input attributes. In this document the term "attributes" is used interchangeably with the term "features."

Explainability of machine learning models and artificial intelligence has recently become a major focus of research. Concerns about biases in ML implementations, including those based on gender or race, and the recognition of the right of people to understand how their personal data is being used, have focused attention on how to provide simple explanations and quantification of how attributes are used by complex ML algorithms. For example, the EU General Data Protection Regulation of 2016 addresses this issue, providing individuals with the right to receive explanations of automated decisions carried out on the basis of their personal data.

Explainability research has moved away from trying to provide a global description of relative attribute importance accurate for all possible sets of input data, which is unlikely to be successful, given the complexity and nonlinearities inherent in most ML approaches, to a local approach of assessing relative attribute importance for the result for a specific set of input data. In the case of molecular tests, this latter approach corresponds to providing a description of the relative importance of the attributes used to the result generated for an individual patient.

One proposal has been to construct a simpler, more interpretable model of a complex ML algorithm which reproduces the results of the full ML algorithm in the vicinity of the particular result we seek to explain. The local interpretable model-agnostic explanation (LIME) approach, see Ribeiro M T, Singh S, Guestrin C (2016). *Why should/trust you? Explaining predictions of any classifier* in Proceedings of the 22nd ACM SIGKDD International Conference on Knowledge Discovery and Data Mining, seeks to generate a model of a ML algorithm which can be easily interpreted and which can reproduce the results of the ML algorithm in the locality of the result to be explained without requiring information about the ML algorithm itself. Only oracle access to the ML algorithm is required—i.e., only results of the ML algorithm for various inputs are necessary and no details of how they are arrived at from the input attributes. However, this approach relies on being able to train simpler, interpretable, locally accurate models in the vicinity of a result to be explained. In the case of binary or categorical tests, there are often large regions in feature space with consistent classifications (e.g. regions of feature space within which all feature values produce the same classification). Hence, locally only one test result can be generated. However, examples of both binary classes or multiple categorical classes are required to train the LIME model and these often do not exist in any sense locally to the sample for which we are seeking to explain the classification. Additionally, many ML models can demonstrate discontinuous behaviors, e.g., change in classification at a decision boundary for a k-nearest neighbor classifier, making it hard or impossible to define locality.

An alternative approach to explainability makes use of game theory concepts developed for determining the equitable distribution of winnings between players working in teams. Parallels between deciding on a fair distribution of winnings between team members in multiplayer games and assessing the relative importance of multiple input attributes to the result of a ML algorithm were observed several years ago. It was proposed that Shapley values (SVs), see Shapley L S (1953). *A Value for N-Person Games.* Contributions to the Theory of Games 2, 307-317, which provide an equitable scheme for dividing game winnings within a team of multiple players, could provide the framework for assigning relative importance of multiple attributes to the result of a ML algorithm. See Štrumbelj E, Kononenko I (2010). *An Efficient Explanation of Individual Classifications using Game Theory.* Journal of Machine Learning Research 11, 1-18; and Štrumbelj E, Kononenko I (2014). *Explaining prediction models and individual predictions with feature contributions.* Knowledge and Information Systems 41, 647-665. SVs assess the contribution of a player to the team's result, or, equivalently, the contributions of an attribute to the algorithm output, by examining the results/algorithm predictions for all possible coalitions of players within the team, or all possible subsets of attributes.

Formally, let us assume that we have a predictor $f(\{S\})$ which depends on a set of attributes $\{S\}$. Further, we assume that we can define the prediction for any subset of attributes, $\{S\}$, contained within a set of all available attributes $\{M\}$. The SV for an attribute j contained in $\{M\}$ is $$\varphi_j = \sum_{\{S\} \subseteq \{M\} \setminus \{j\}} \frac{|S|!(|M|-|S|-1)!}{|M|!} (f(\{S\} \cup \{j\}) - f(\{S\}))$$

SVs satisfy several axioms which guarantee that SV explanations have some properties that are logically consistent and aligned with human intuition. These properties include: efficiency (the entirety of the prediction result is distributed among the attributes), symmetry (attributes contributing in an equal manner are guaranteed to be assigned equal SVs), dummy player (attributes with definitively zero contribution to classification are assigned a SV of 0), and linearity (the SVs for a prediction defined as the sum of two separate predictions is the sum of the SVs calculated individually for the two separate predictions).

Unfortunately, heretofore the exact evaluation of SVs for ML algorithms using more than a handful of attributes (under 50) is generally unfeasible. There are two main issues that arise:

1. The requirement to sum over all possible subsets of attributes.

This is a task of exponential complexity. For a set of attributes of size $|M|$, there are $2^{|M|}-1$ subsets that we have to sum over to find the SV for each member of $\{M\}$. In clinical diagnostics the value of $|M|$ can be on the order of 100 or even 1000, and thus the complexity and computer processing power required to sum over all possible subsets of attributes becomes prohibitively expensive or too time consuming, even using modern general purpose computer processors.

2. The need to be able to calculate the prediction of the complex ML model using only a subset of attributes.

This second problem is multi-faceted. First, one needs to be able to define what we mean by a prediction from the complex ML model with a smaller subset of features. Take a simple example of a k-nearest neighbor algorithm based on eight features. The direct interpretation of the ML model based on a subset of the eight features, would be a k-nearest neighbor algorithm trained on the same reference set as the original 8-feature model, using the same k, but using the smaller subset of features. As a k-nearest neighbor algorithm does not require a training phase, this could be implemented, provided that the classifier reference set were available. (Note that with only oracle access, this would not be possible, even for this simple example.) However, many complex ML algorithms require training to define model parameters and this would need to be repeated for each possible subset of attributes. This would quickly become compute-time prohibitive for complex models with even small numbers of attributes and even for simpler models that use larger numbers of attributes.

Several approaches have been proposed to alleviate these two issues. Kernel SHAP (see Lundberg S M, Lee S (2017). *A Unified Approach to Interpreting Model Predictions*. In Advances in Neural Information Processing Systems. Curran Associates Inc.) and extensions (see Aas K, Jullum M, Løland A (2020). *Explaining Individual Predictions When Features are Dependent: More Accurate Approximations to Shapley values*. arXiv:1903.10464v3 [stat.ML]), have been proposed to attempt to circumvent the need to retrain models on attribute subsets. However, these approaches break the correlation structures between attributes, lead to violation the exact SV axioms and can lead to results that can be counterintuitive and misleading. See Aas et al, supra, and Merrick L, Taly A (2020). *The Explanation Game: Explaining Machine Learning Models using Shapley values*. arXiv: 1909.08128v3 [cs.LG]. Furthermore, there are no methods to understand how close the results are to the exact SVs. The first issue, summation of an exponential number of attribute subsets, has been addressed using sampling methods. See Shapley and Lundberg et al., supra and Jia R, Dao D, Wang B, Hubis F A, Hynes N, Gurel N M, et al. *Towards Efficient Data Valuation Based on the Shapley Value*. Proceedings of the 22nd International Conference on Artificial Intelligence and Statistics (AIS-TATS) 2019. PMLR: Volume 89. These approaches are based on the observation that not all attribute subsets contribute equally to the Shapley sum and hence, sampling those subsets that contribute most at the expense of subsets contributing little, can lead to an approximation to the exact SV in less than exponential time. Monte Carlo-based sampling schemes should produce well-controlled approximations to exact SVs, although very little work has been done to characterize the convergence of these methods to exact SVs.

Further background information on interpretable machine learning models and Shapley values is found in the on-line publication of Christoph Molnar, *Interpretable Machine Learning, A Guide for Making Black Box Models Explainable*, chapter 5.9, available at https://christophm.github.io/interpretable-ml-book/shapley.html, first published online on Nov. 20, 2020.

To summarize the above, Shapley values have become an important tool to further the goal of explainability of ML models. Molecular diagnostic tests typically seek to leverage information from hundreds or thousands of attributes, often using training sets with fewer instances. However, the computational load of exact SV calculations increases exponentially with the number of attributes. Hence, the calculation of SVs for models incorporating large numbers of interpretable attributes (>50), for example those used in clinical diagnostics, is problematic at best or in some cases, is not technically feasible.

SUMMARY

We demonstrate that it is possible to evaluate SVs efficiently and relatively quickly (in "polynomial time" in language of computer science and complexity theory) using the architecture of a ML model which is designed for robust molecular and diagnostic test generation. Application of this method to real-world data and clinically validated molecular and diagnostics tests indicates that SVs has several practical advantages and uses. For one, the calculation of the SVs and providing them in conjunction with classification prediction makes the ML model interpretable or understandable, and the model is no longer a "black box." This, in turn, increases confidence in the model's prediction and fosters acceptance of the model and the predictions within the relevant scientific and medical community. Furthermore, the SVs can be used to detect patient subgroups or molecular phenotypes within classes of patients identified by the ML model, which provides the basis for hypotheses for translational biology research. Additionally, the SVs associated with particular test classifications for a particular patient can lead to suggestions for treatment decisions or point to areas for further diagnostic testing for the patient.

The architecture of a ML model which we use for molecular and diagnostic test generation, and which we have discovered is ideally suited to calculation of SVs, is referred to herein as the "Diagnostic Cortex®" approach. This architecture is described in the prior patent literature of Biodesix, including U.S. Pat. No. 9,477,906, the content of which is incorporated by reference, and Röder et al., *A Dropout-Regularized Classifier Development Approach Optimized for Precision Medicine Test Discovery from Omics Data*, BMC Bioinformatics. 2019; 20:325 and Röder et al., *Robust Identification of Molecular Phenotypes using Semi-Supervised Learning*, BMC Bioinformatics. 2019; 20:273.

Examples of application of that architecture to generate specific molecular diagnostic tests include U.S. Pat. Nos. 10,950,348, 10,037,874, 10,489,550, and still other patents of the assignee Biodesix, Inc. In essence, a classifier in accordance with this architecture is configured as a logistical combination of atomic or "mini-classifiers" (classifiers using a small number of individual attributes, such as 1, 2, or 3, to generate a classification result, using a k-nearest neighbor classification algorithm), with dropout regularization, that is, composed of an average over many dropout iterations each of which is a coalition of a subset of the total number of available attributes.

By virtue of this architecture, it means that calculation of Shapley values for the Diagnostic Cortex classifier trained on the same reference set using a smaller number of attributes can be obtained without the need for classifier retraining. This will be explained in further detail below. However, the principle is simple: one observes that a dropout iteration that is a coalition of a subset of features, {S}, created and trained for the model using the entire set of features {M}, is also an allowable dropout iteration for any subset of {M} that includes {S}. This observation removes the need for classifier retraining (point 2 above) and so allows the calculation of approximations to SVs using Monte Carlo-based sampling to address point 1, or even an exact calculation of SVs.

In one specific aspect, we describe a method for interpreting a prediction as to a patient made by a trained machine learning classifier, wherein the machine learning classifier is arranged as a logistical combination of atomic classifiers with drop-out regularization. The method includes steps of:

(a) obtaining values for a set of attributes associated with the patient from an electronic health record of the patient or from one or more measurements obtained from the patient or sample obtained therefrom, or both, (b) with a programmed computer, classifying the set of values with the trained machine learning classifier and generating the prediction;

(c) with the programmed computer, generating an explanation of the prediction by calculating the relative contribution of some or all of the attributes to the prediction; wherein the calculating step comprises either calculating exactly or estimating the Shapley values for the attributes, and (d) generating a report comprising (1) the prediction, (2) data representing the calculation of the relative contribution of some or all of the features from step (c), either in text or graphical format, or both, and (3) optionally comments on (1) and/or (2).

In one embodiment step (a) includes a step of performing a physical measurement on a sample obtained from the patient, such as mass spectrometry on a blood-based sample or conducting a genomic or proteomic assay. As another embodiment, the patient is a hospitalized patient and the attributes take the form of clinical and demographic data and findings obtained at admission to a hospital and wherein the prediction comprises a prediction of risk of future adverse event for the patient while hospitalized. For example, the patient is infected with the SARS-Cov-2 virus and the predicted adverse event is intubation, transfer to the ICU, or development of Acute Respiratory Distress Syndrome. This embodiment is an example where the trained machine learning classifier takes the form of a combination of trained decision trees and the logistical combination of atomic classifiers with drop-out regularization.

In one possible implementation, the classifier takes the form of a hierarchical arrangement of a binary classifier and one or more child classifiers, and wherein the method includes the step of calculating Shapley values for one or more of the attributes for the predictions generated by both the binary classifier and the one or more child classifiers.

As will be explained below, in one embodiment Shapley values for the one or more of the attributes are calculated by a Monte Carlo sampling method and calculated in accordance with equation 2.8 below. Alternatively, the Shapley values for the one or more of the attributes are calculated exactly, without using Monte Carlo sampling methods, using equations 5.2 and 5.3 and 5.4 or the equivalent, explained below.

In one possible embodiment, the report of step d) includes a graphical plot of the Shapley values for some or all of the attributes, such as a radar plot or Violin plot.

In another aspect, a method for generating an explainable machine learning model in clinical diagnostics is provided. The method includes steps of:

a) conducting a physical measurement process on a multitude of biological samples obtained from humans, the samples and associated clinical data forming a classifier development set, thereby obtaining a set of values for a multitude of attributes for each member of the development set, b) storing the set of values in computer memory;

c) with a computer, training a classifier arranged as a logistical combination of atomic classifiers with dropout regularization from set of feature values for the development set; and d) using a Monte-Carlo sampling method to sample the classification of subsets of the attributes to calculate Shapley values indicating the relative importance of some or all of the attributes to classifications of the development set produced by the classifier trained in step c) without retraining the classifier. In one embodiment, the attributes comprise mass spectrometry feature values in the form of integrated intensity values at specific m/Z ranges. Alternatively, the attributes take the form of genomic or proteomic data, such as expression levels of particular proteins. In one embodiment, the number of attributes is at least 50. Alternatively, the number of attributes is at least 100.

In another aspect, a method for generating an explainable machine learning model in clinical diagnostics is disclosed. This method includes the steps of:

a) conducting a physical measurement process on a multitude of biological samples obtained from humans, the samples and associated clinical data forming a classifier development set, thereby obtaining a set of values for a multitude of attributes for each member of the development set;

b) storing the set of feature values in computer memory;

c) with a computer, training a classifier arranged as a logistical combination of atomic classifiers with dropout regularization from set of values for the development set; and d) calculating Shapley values exactly indicating the relative importance of some or all of the attributes to classifications of the development set produced by the classifier trained in step c) without retraining the classifier, wherein the exact calculation is performed using equations 5.2 and 5.3 and 5.4 or the equivalent.

In one embodiment, the attributes comprise mass spectrometry feature values in the form of integrated intensity values at specific m/Z ranges. Alternatively, the attributes take the form of genomic or proteomic data, such as expression levels of particular proteins. In one embodiment, the number of attributes is at least 50. Alternatively, the number of attributes is at least 100.

The type of test or prediction that is made from the trained machine learning classifier in clinical diagnostics is not particularly important and can vary widely, and will depend on what clinical question the classifier is trained to address. In one possible implementation, the patient is a hospitalized patient and wherein set of feature values comprises clinical and demographic data and findings obtained at admission to a hospital and wherein the prediction comprises a prediction of risk of future adverse event for the patient while hospitalized. As one example, the patient is infected with the SARS-Cov-2 virus. As another alternative, the patient is a cancer patient and the classifier predicts, e.g., risk of recurrence of the cancer or likelihood of benefit of a particular therapy or combination of therapies.

BRIEF DESCRIPTION OF THE DRAWINGS

FIG. 3C is a flow chart showing how Shapley values are evaluated using the method of Jia et al. with Monte-Carlo sampling (section 2.2).

In FIG. 5, the SVs are plotted simultaneously with attribute values. In particular, FIG. 5 shows a scatter plot of SV and C-reactive protein (CRP) value with color coding by corresponding classification (lower risk and higher risk). We see that generally lower values of CRP correspond to lower risk of developing ARDS (Acute Respiratory Distress Syndrome)

in a hospitalized COVID-19 patient. The plot of FIG. 5 (or the equivalent) could be provided in a report, for a physician caring for the patient.

FIGS. 6A-8B are plots of SVs for each patient and feature for each individual classifier that makes up the hierarchical tests predicting unfavorable outcomes in hospitalized COVID-19 patients. SVs that are negative correspond to a classification of higher risk (higher risk classification corresponds to −1 and lower risk classification corresponds to +1), and larger magnitude implies a greater share of contribution from that attribute.

Figure 6A:
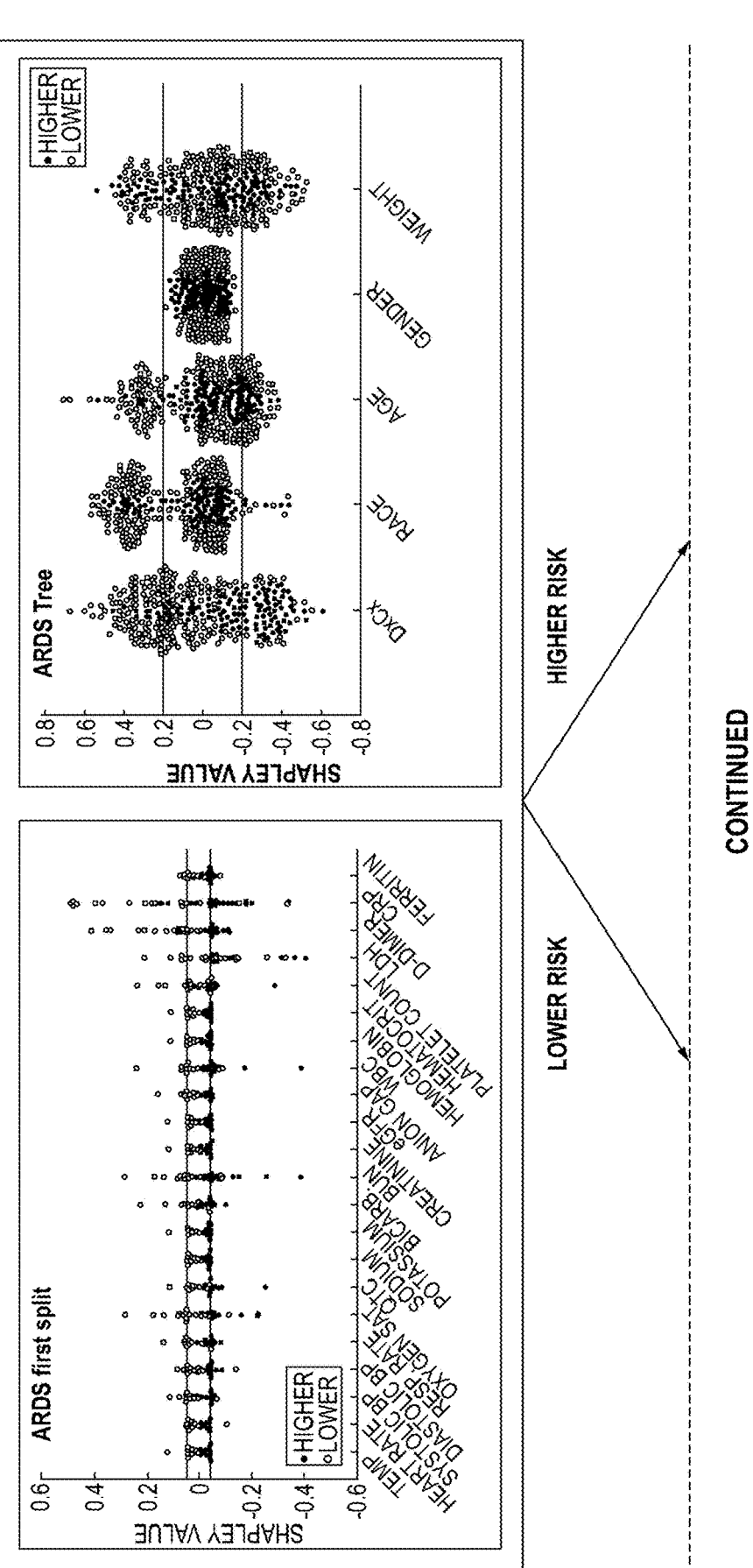
Figure 6B:
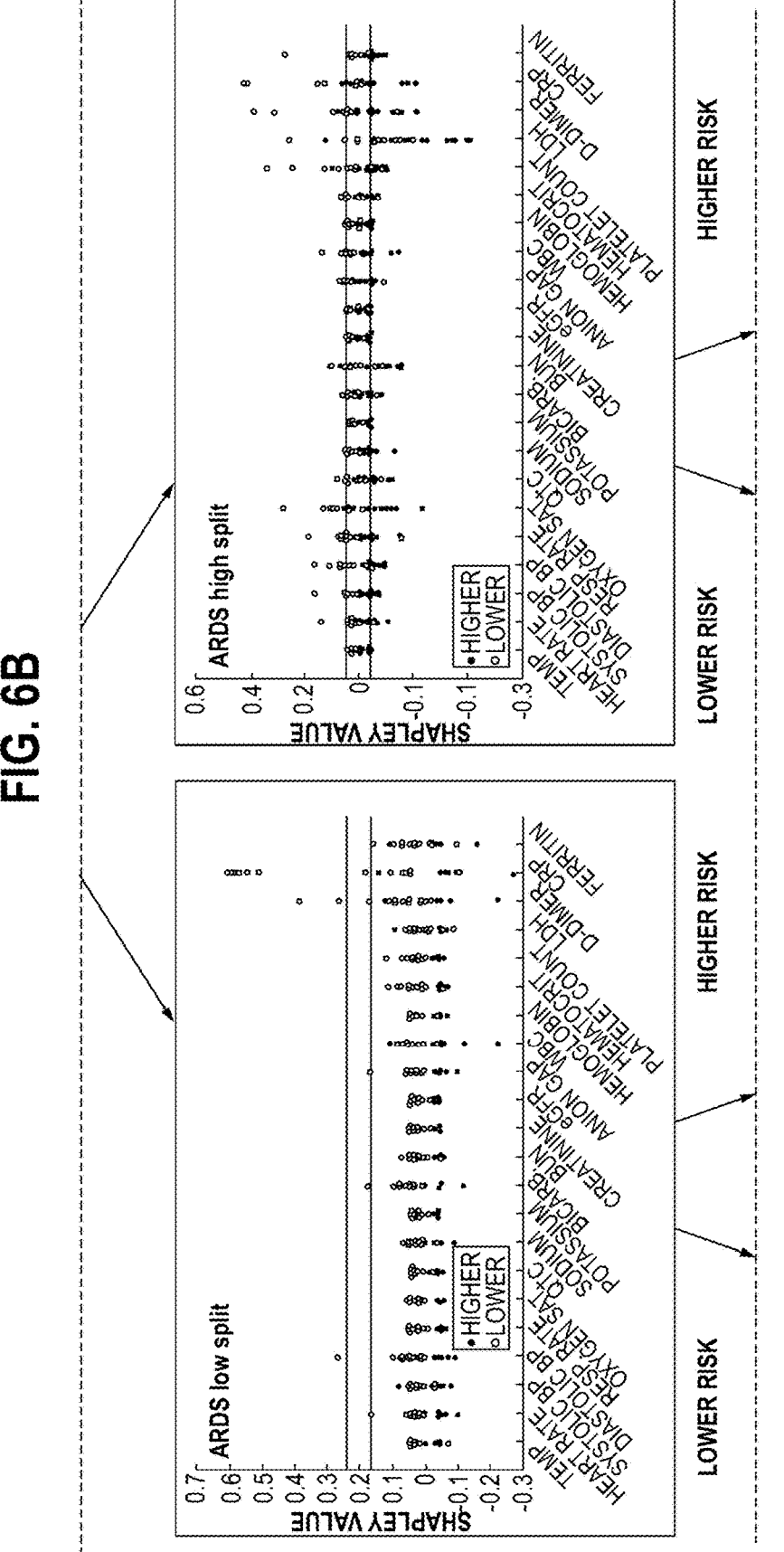
Figure 6C:
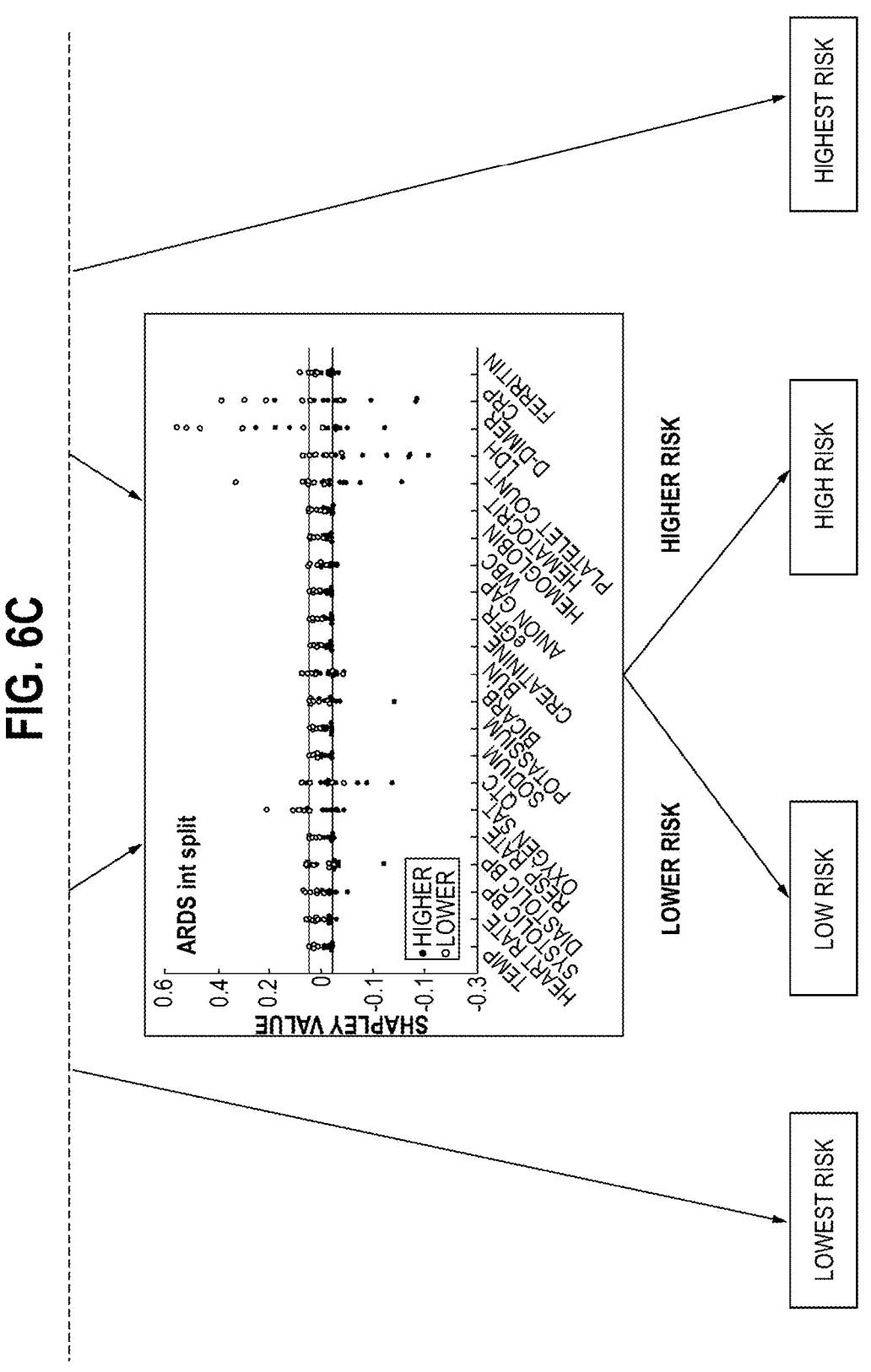

In FIG. 6, consisting of FIGS. 6A, 6B and 6C, the test is predicting risk of developing ARDS.

Figure 7A:
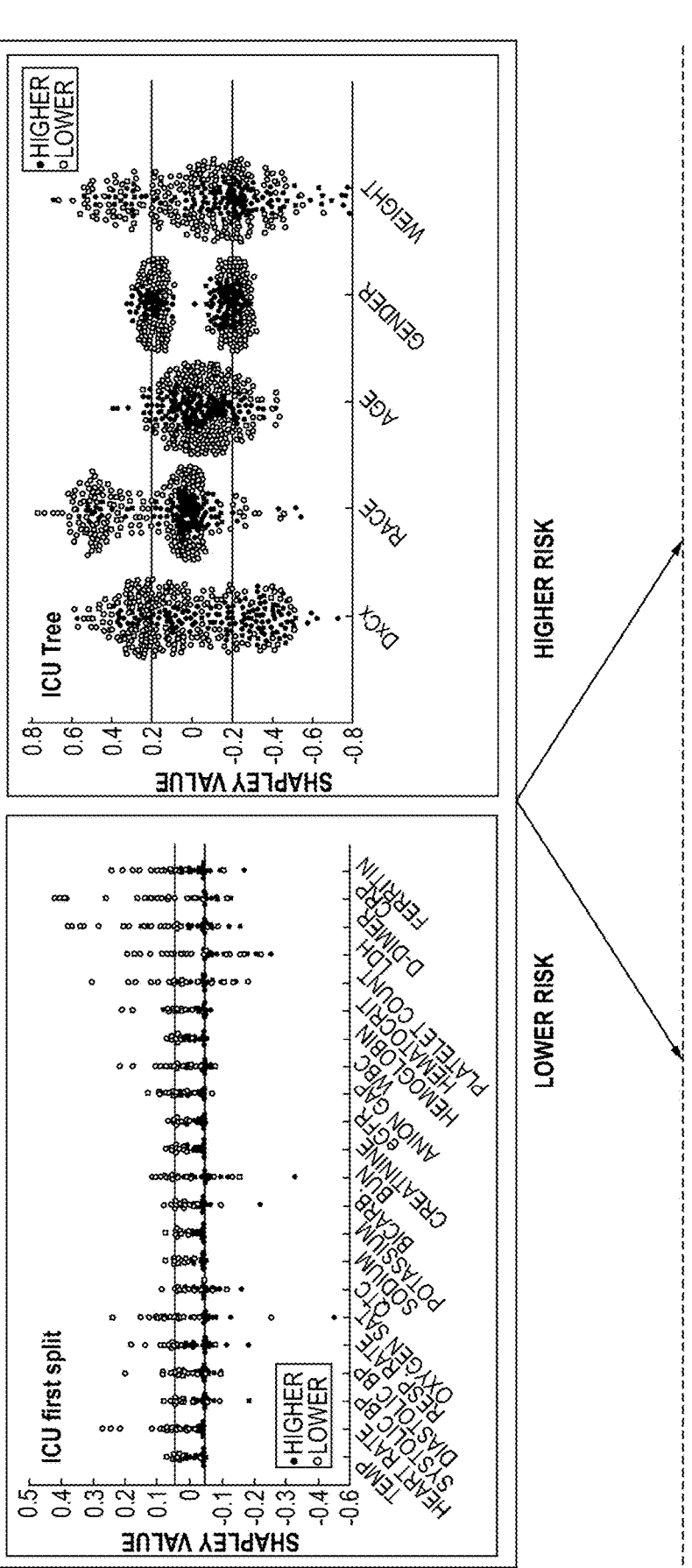
Figure 7B:
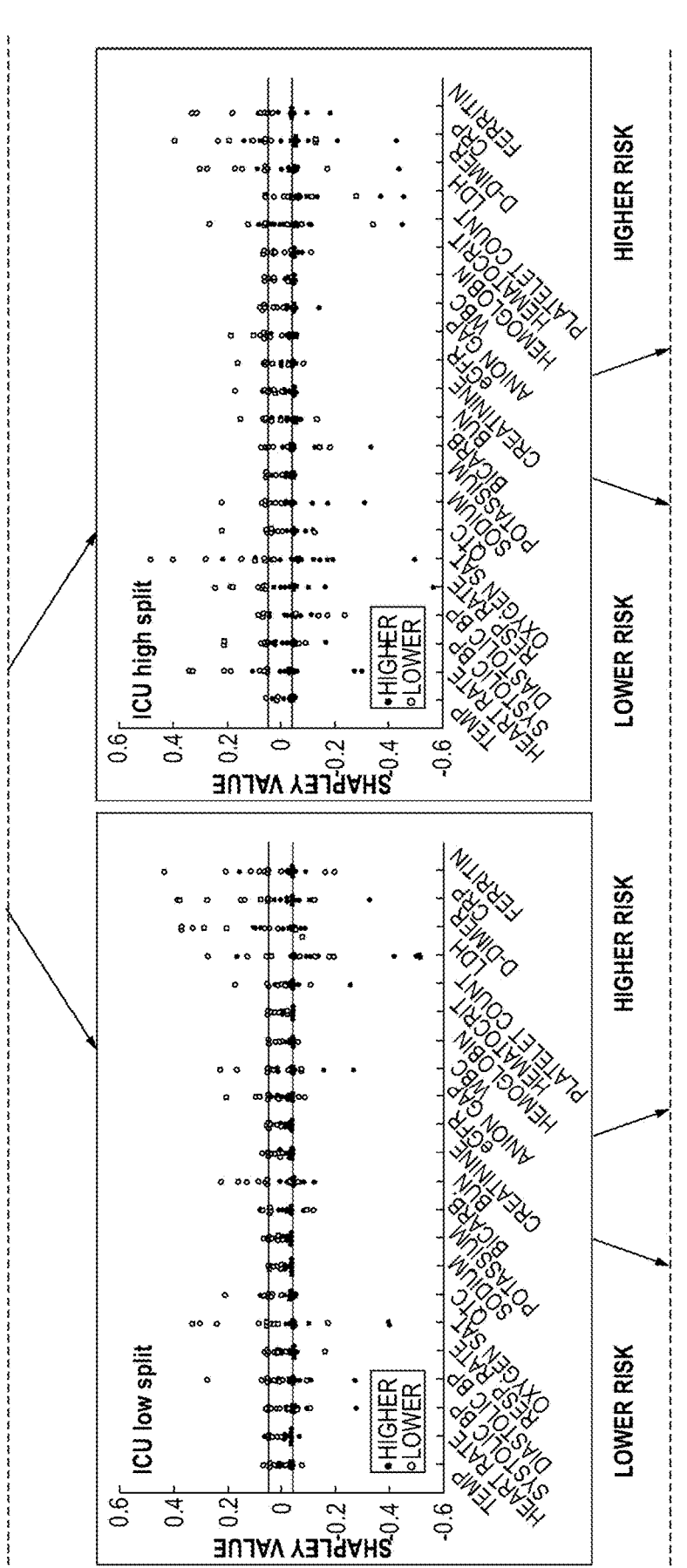
Figure 7C:
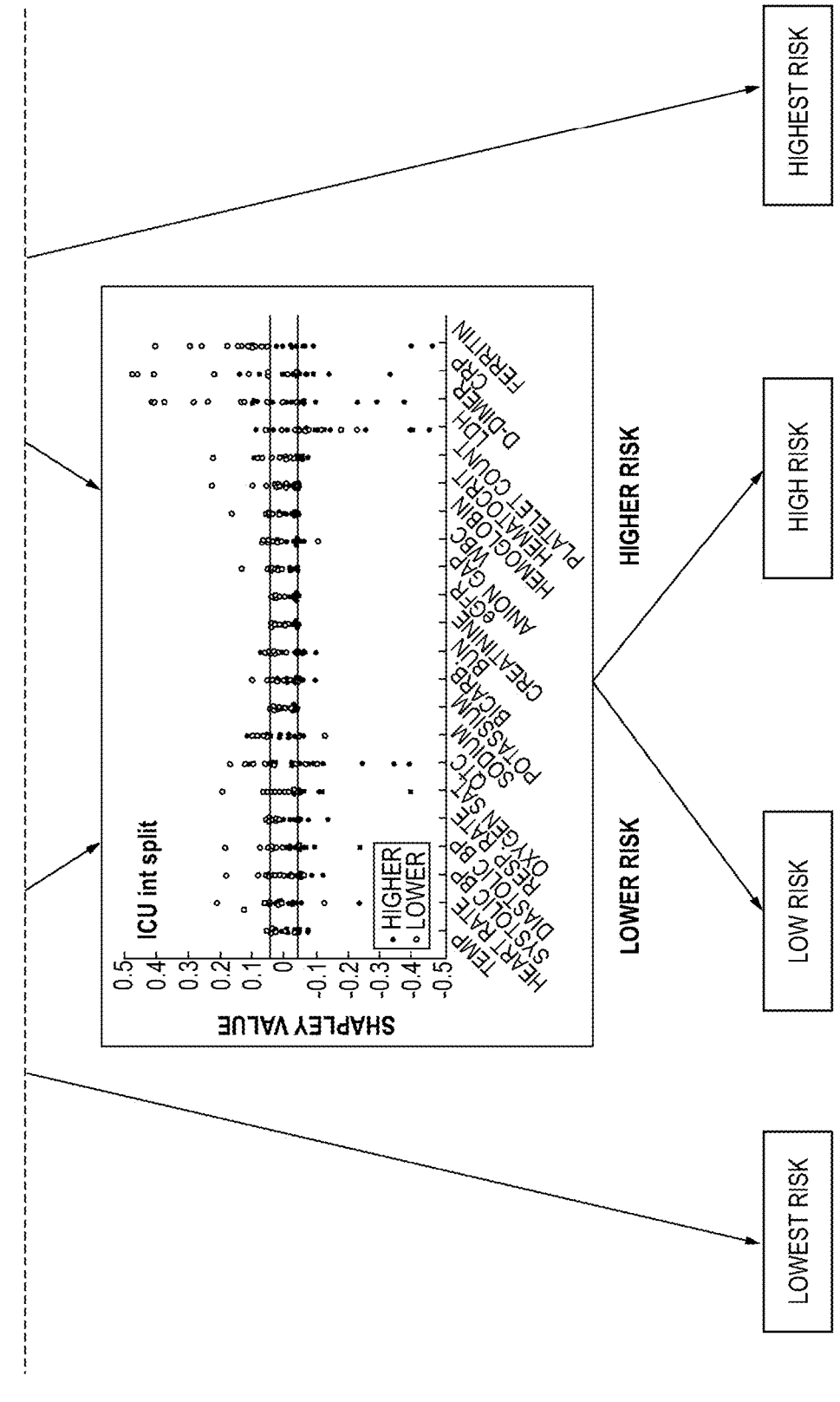

In FIG. 7, consisting of FIGS. 7A, 7B and 7C, the test is predicting risk for admission to the ICU.

Figure 8A:
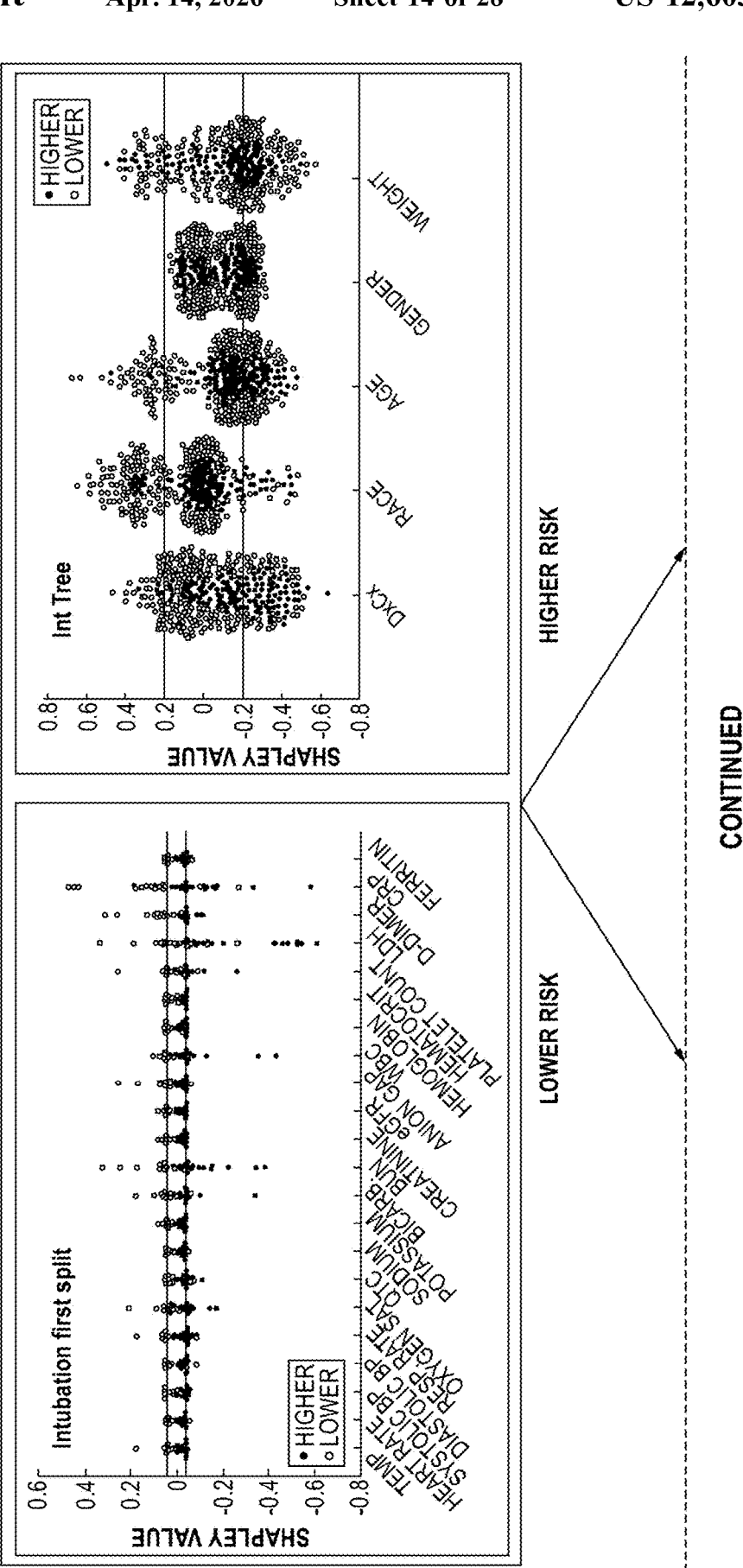
Figure 8B:
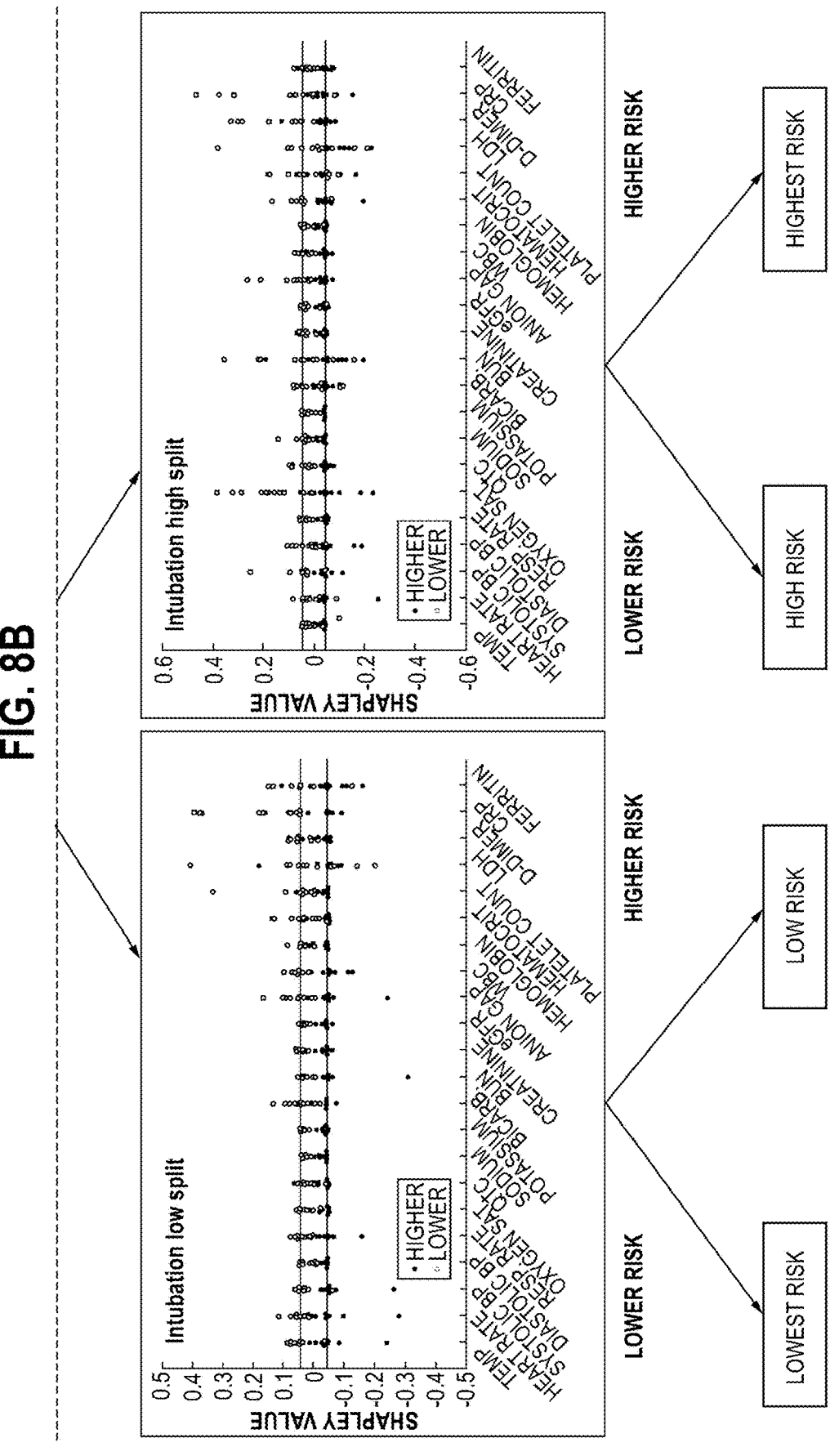

In FIG. 8, consisting of FIGS. 8A and 8B the test is predicting risk of intubation.

Figures 1, 2:
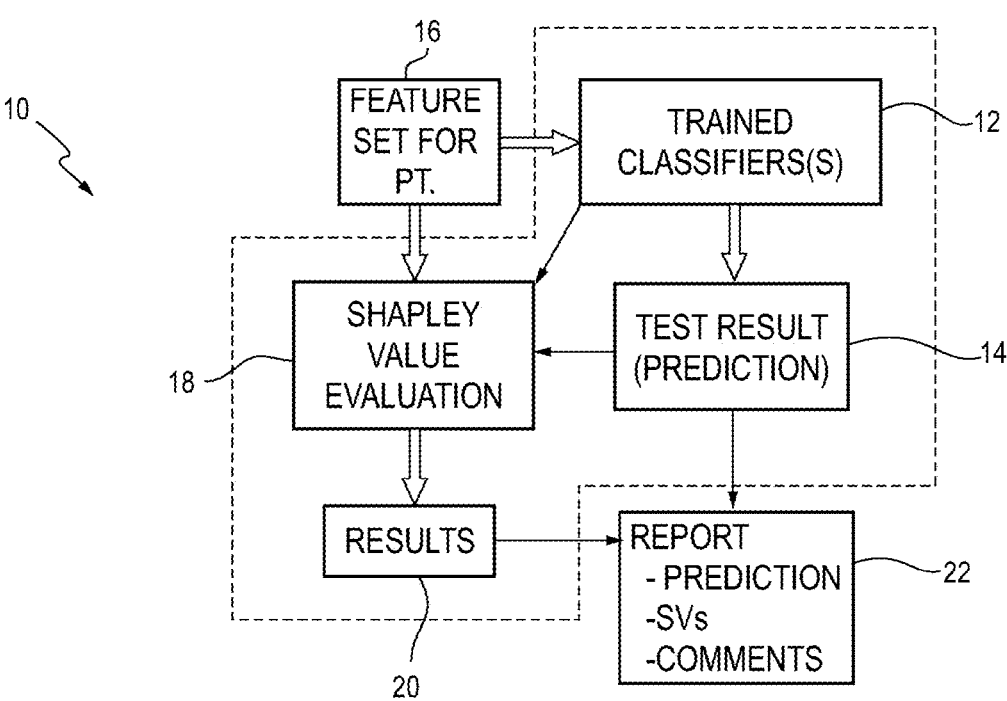
FIG. 1 is a high level description of a computer processing system which implements a ML classifier to generate a prediction in accordance with a diagnostic test for a patient and calculates Shapley values providing explainability to the prediction in accordance with the present disclosure.
FIG. 2 is an illustration of several possible physical process steps which could be used to generate the set of features (or "attributes") which are used for classification in accordance with the system of FIG. 1.
Figure 9:
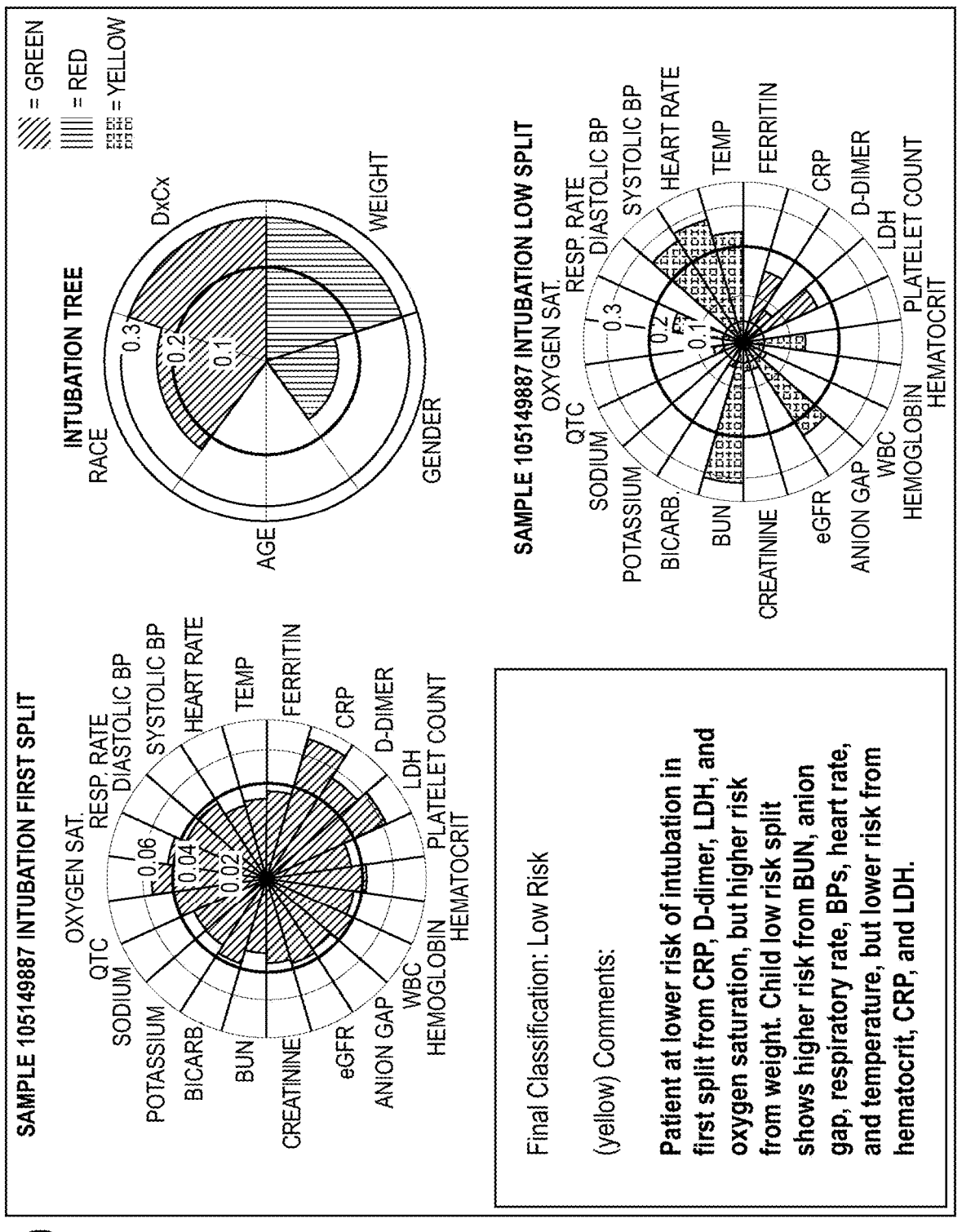

FIG. 9 is an example of a report generated in accordance with FIG. 1 which could be provided to a patient or the patient's physician. The report provides (1) the prediction in accordance with the molecular or diagnostic test developed in accordance with the Diagnostic Cortex architecture (see FIG. 4 and the above discussion), (2) data representing the calculation of the relative contribution of some or all of the features which contributed to the prediction, i.e., the SVs, in this case in graphical format (so-called "radar plots") and (3) comments on the prediction and the SVs. In the present example, the test is predicting risk of intubation for a hospitalized COVID-19 patient made from attributes in the form of basic patient characteristics, laboratory findings and clinical data including findings obtained at hospital admission.

Figure 10:
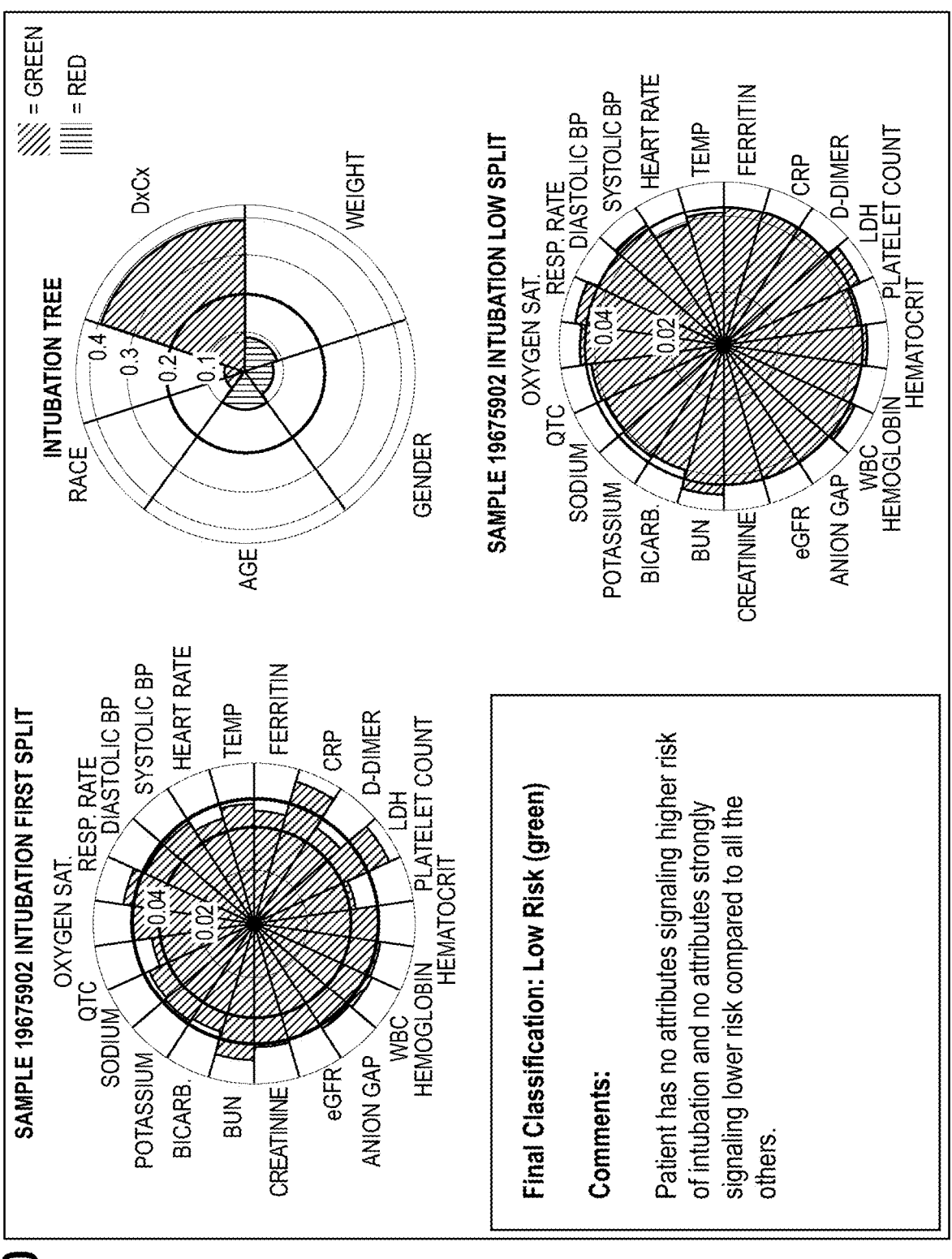

FIG. 10 is another example of a report similar to that of FIG. 9, including the risk prediction (intubation), the radar plots showing the SVs for certain features, and commentary on the prediction and the calculated SVs.

Figure 11:
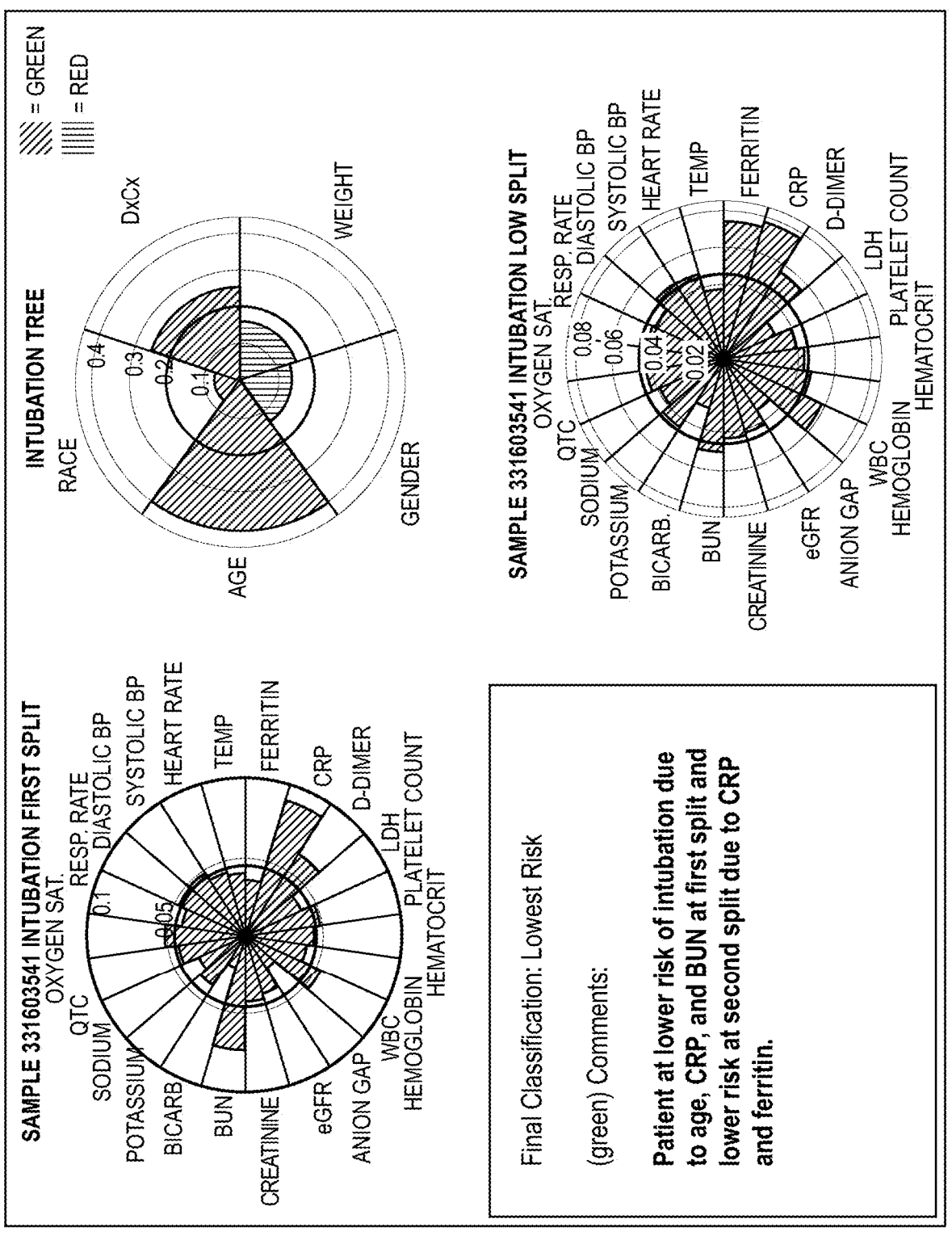

FIG. 11 is another example of a report similar to that of FIG. 10, including the risk prediction (intubation), the radar plots showing the SVs for certain features, and commentary on the prediction and the calculated SVs.

Figure 12:
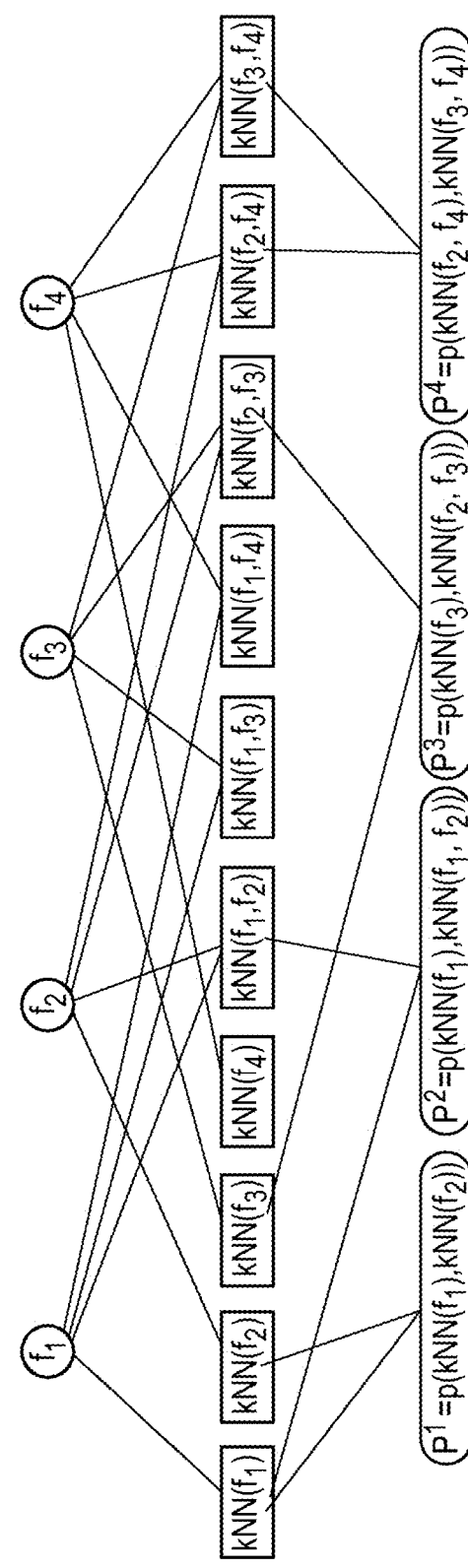

FIG. 12 is an illustration of a simplified Diagnostic Cortex master classifier constructed from 4 features indicated by the circles in the top row. All ten possible singles and pairs are input into respective mini-classifiers, kNN's, shown in boxes in the second row. Four drop-out iterations are shown in the bottom row, where $p(x, y)=(1/(1+exp(-(\beta_0+\beta_1x+\beta_2y)))$ where the $\beta_i$ are the logistic regression coefficients generated in training.

Figure 13:
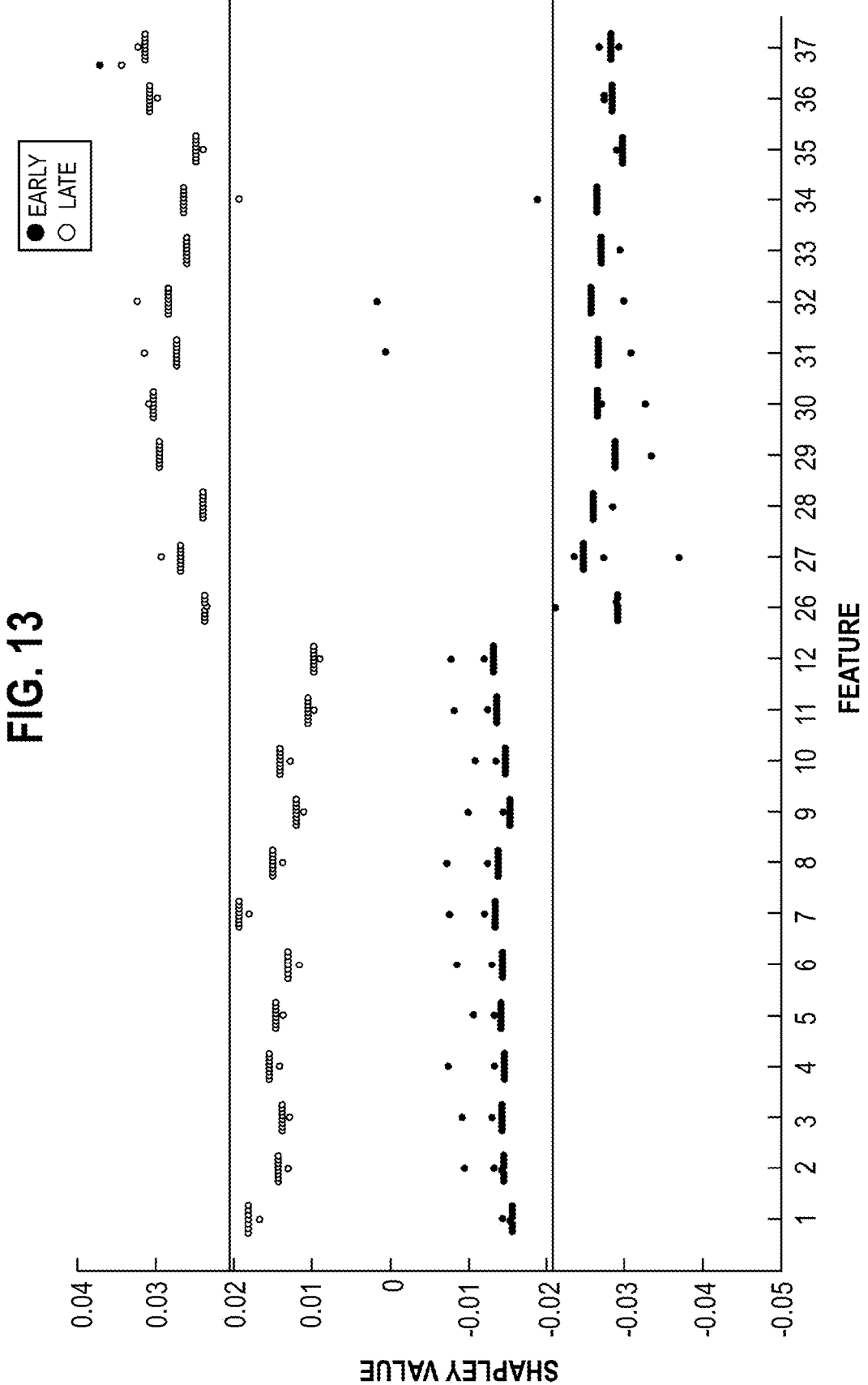

FIG. 13 is a Violin plot of Shapley values for a validation set of 20 samples (10 per phenotype) for a synthetic data model. The test development set and validation set had 24 features (12 non-informative with $\mu=0$, uncorrelated, 12 informative with $\mu=5$ with random correlations), 120 samples (60 per phenotype) were used as the development set, number of dois (drop out iterations)=10,000, and leave-in number=10 averaging over 315 master classifiers. Shapley values were estimated with 1M Monte-Carlo subsets.

Figure 14:
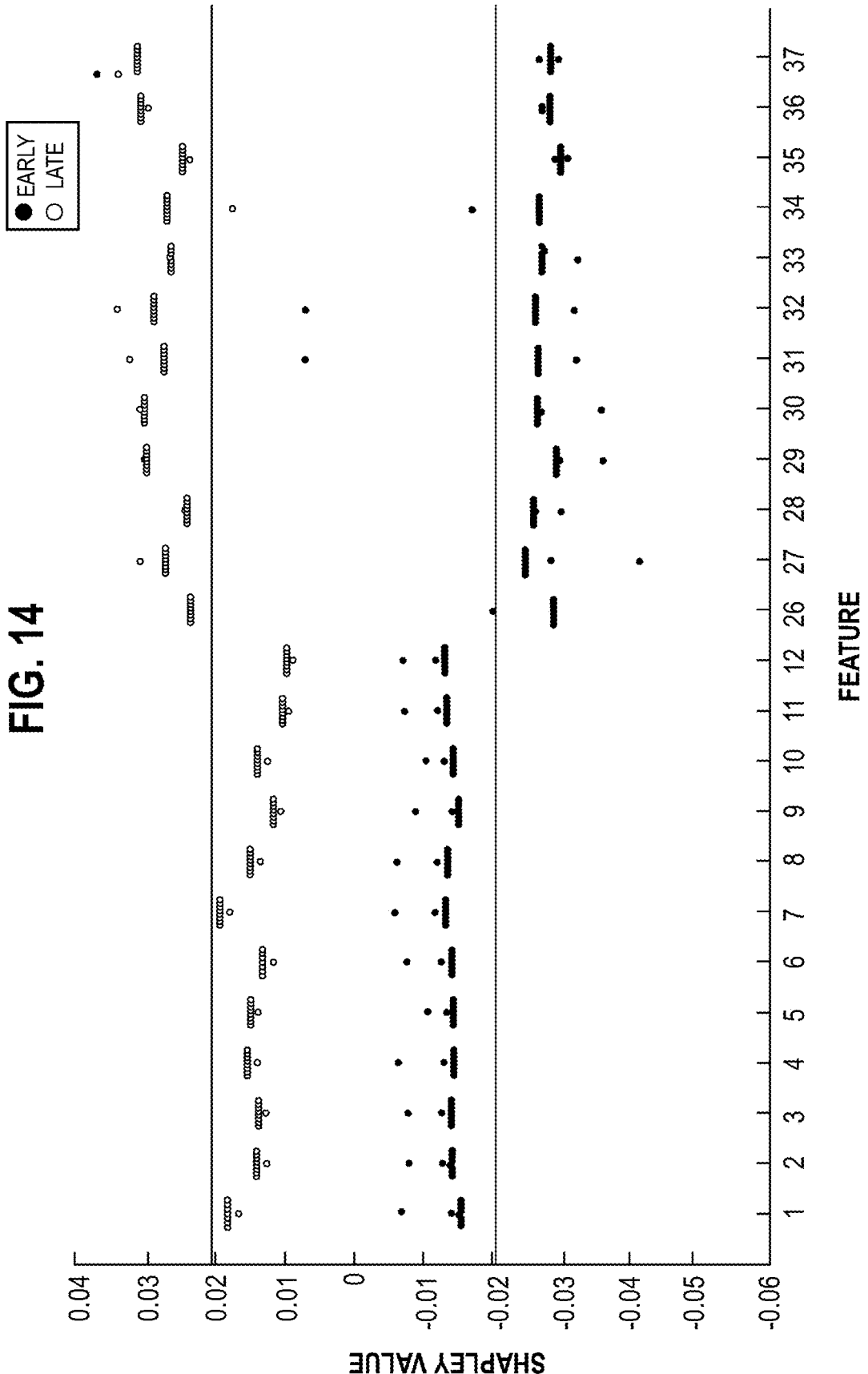

FIG. 14 is a Violin plot of Shapley values for the data model referenced in FIG. 13 but with 100,000 drop out iterations. By comparing FIGS. 14 and 13 we see that changing the number of drop out iterations from 10,000 to 100,000 does not change the Shapley values much at all.

Figure 15:
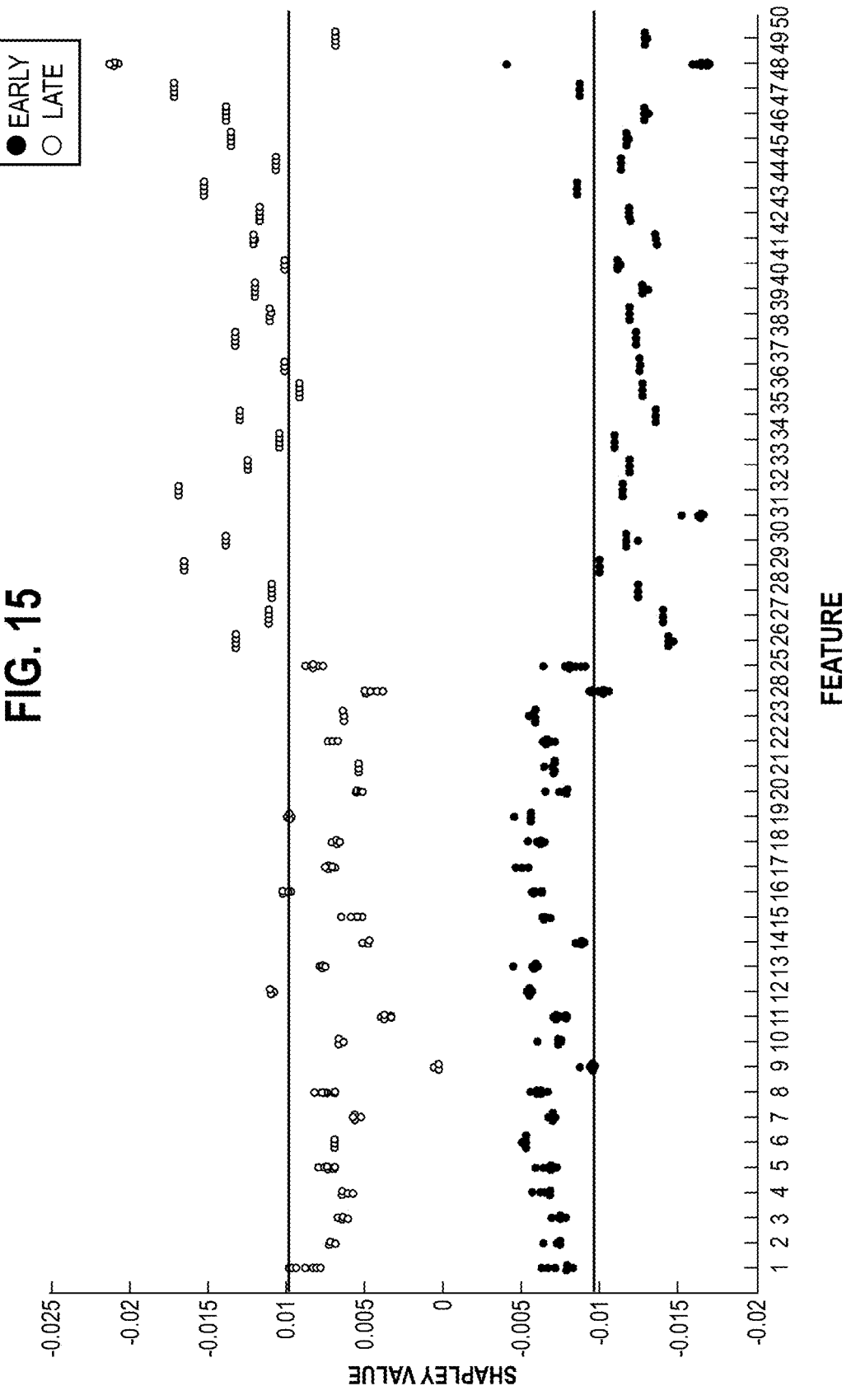

FIG. 15 is a Violin plot of Shapley values for a validation set of 20 samples (10 per phenotype) for a synthetic data model. The test development set and validation set had 50 features (25 non-informative with $\mu=0$ uncorrelated, 25 informative with $\mu=5$ uncorrelated, 120 samples (60 per phenotype) were used as the development set, number of dois=10,000, and leave-in number=10 averaging over 315 master classifiers. Shapley values were estimated with 1M Monte-Carlo subsets.

Figure 16:
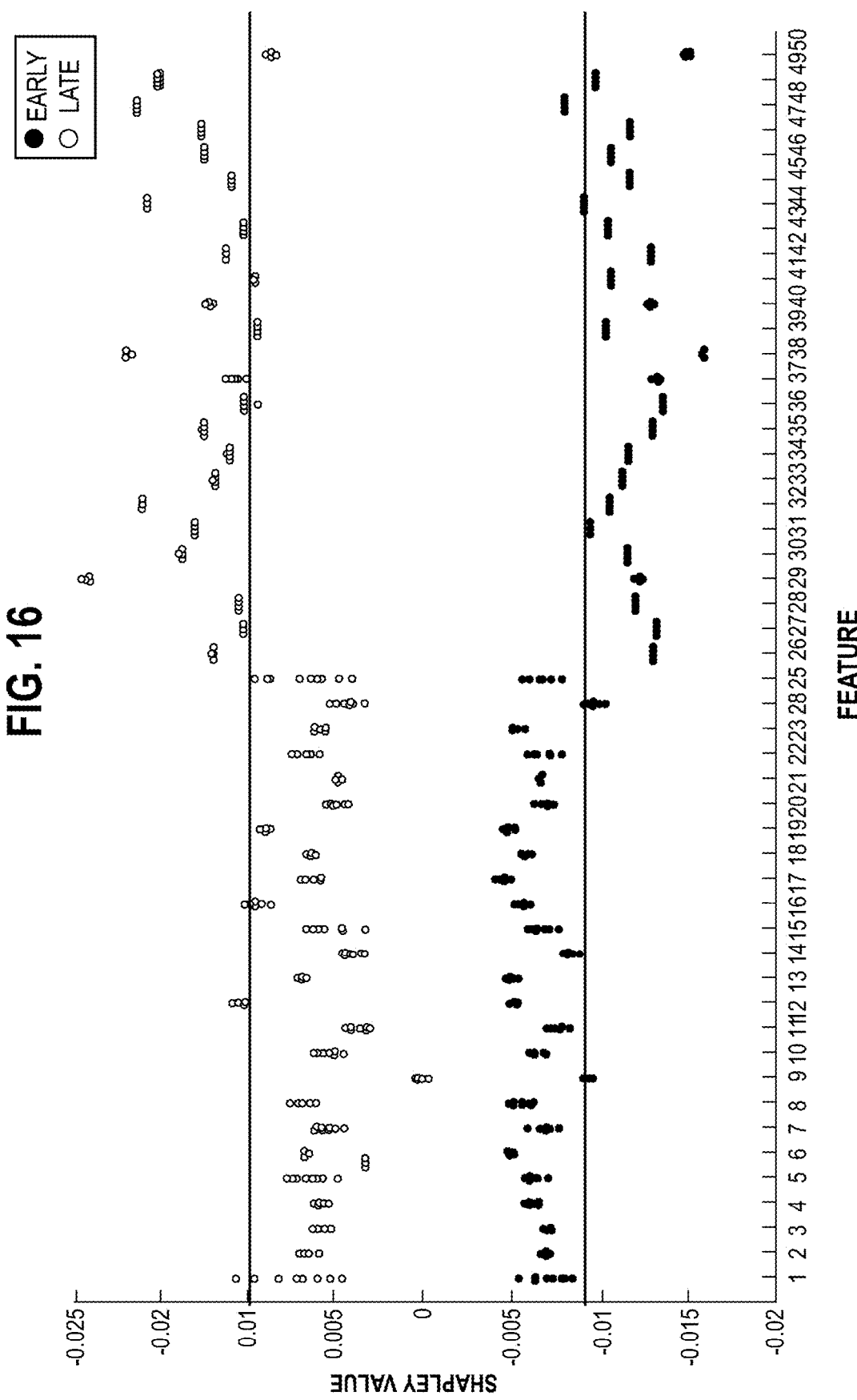

FIG. 16 is a Violin plot of the SVs for a validation set of 20 samples for the synthetic data model described in FIG. 15 but with random correlations between informative features. Together, FIGS. 15 and 16 demonstrate that, for un-informative features there is little difference in Shapley values between no correlation (FIG. 15) and random correlations (FIG. 16). Even non-informative features have a finite, non-zero value, reflecting the coalition structure of the Diagnostic Cortex architecture (uninformative features are paired with informative ones in the mini-classifiers and dois and theoretically uninformative features may have some utility for classification in the given development set). The relative importance of informative features can depend on correlation, see e.g. the relative importance of features 49 and 50 in FIG. 15 and FIG. 16.

Figure 17:
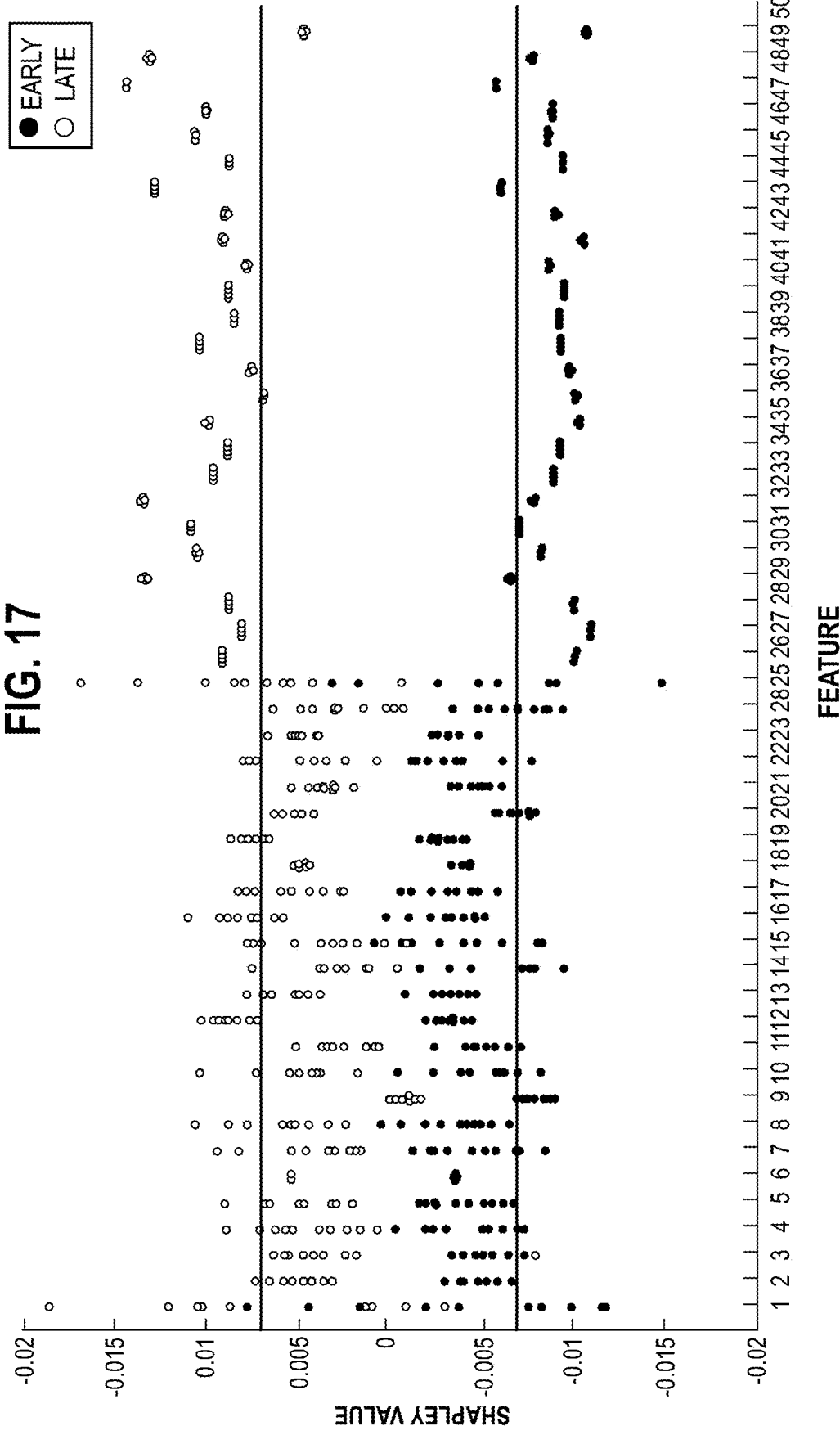

FIG. 17 is a Violin plot of Shapley values for a validation set of 20 samples (10 per phenotype) for a synthetic data model. The test development set and validation set had 50 features (25 non-informative with μ=0 uncorrelated, 25 informative with μ=5 perfectly correlated), 120 samples (60 per phenotype) were used as the development set, number of dois=10,000, and leave-in number=10 averaging over 315 master classifiers. Shapley values were estimated with 1M Monte-Carlo subsets.

Figure 18:
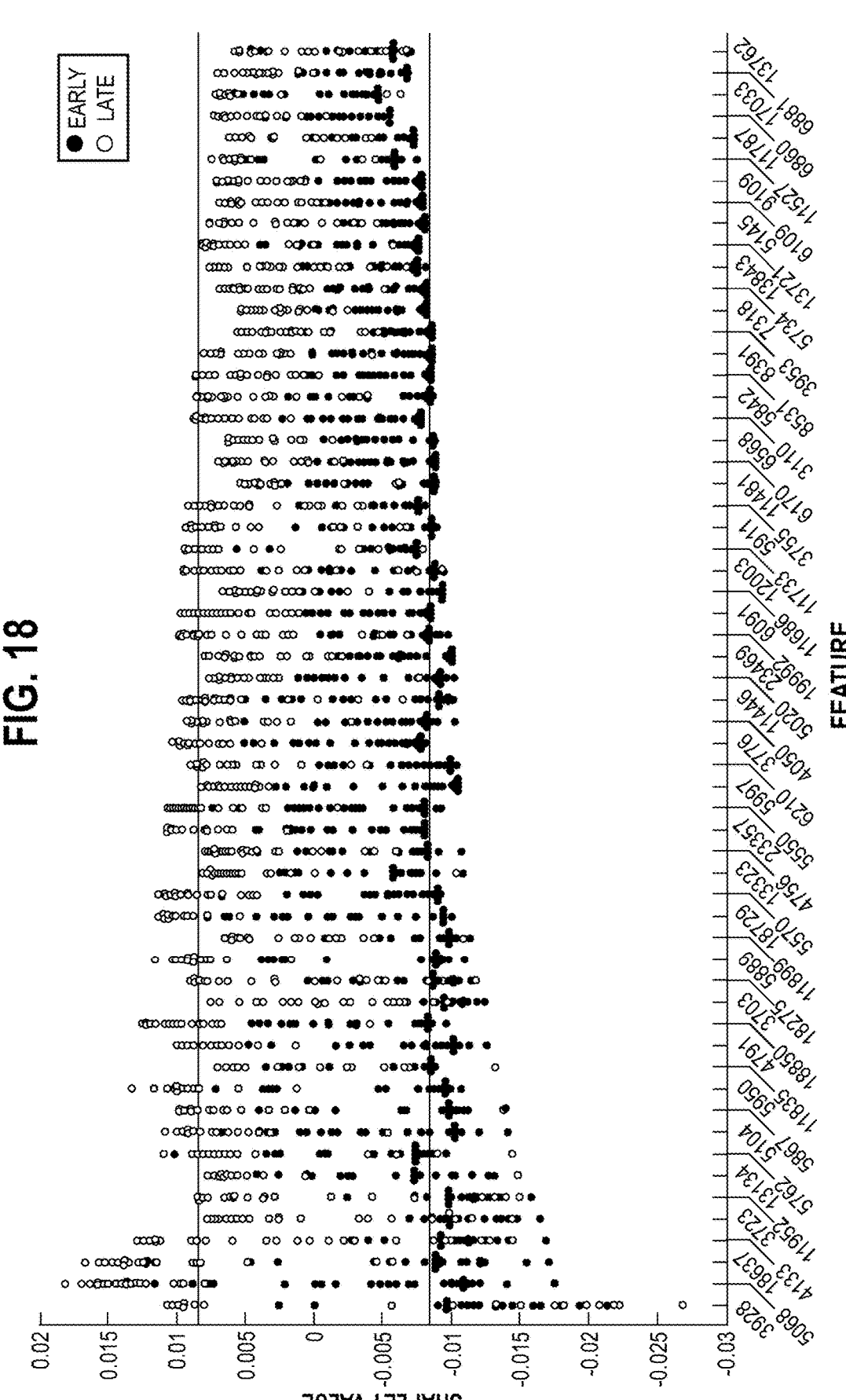

FIG. 18 is a Violin plot of Shapley values for the molecular diagnostic test described in U.S. Pat. No. 10,007,766 referred to "BDX008" from a particular sample set (see Example 1, thereof, classifier "IS2"). Shapley values were estimated using 5M Monte-Carlo subsets. This test predicts cancer patient benefit from an antibody drug blocking ligand activation of the T-cell programmed cell death 1 (PD-1) checkpoint protein from mass spectrometry data of a blood sample from the patient.

Figure 19A:
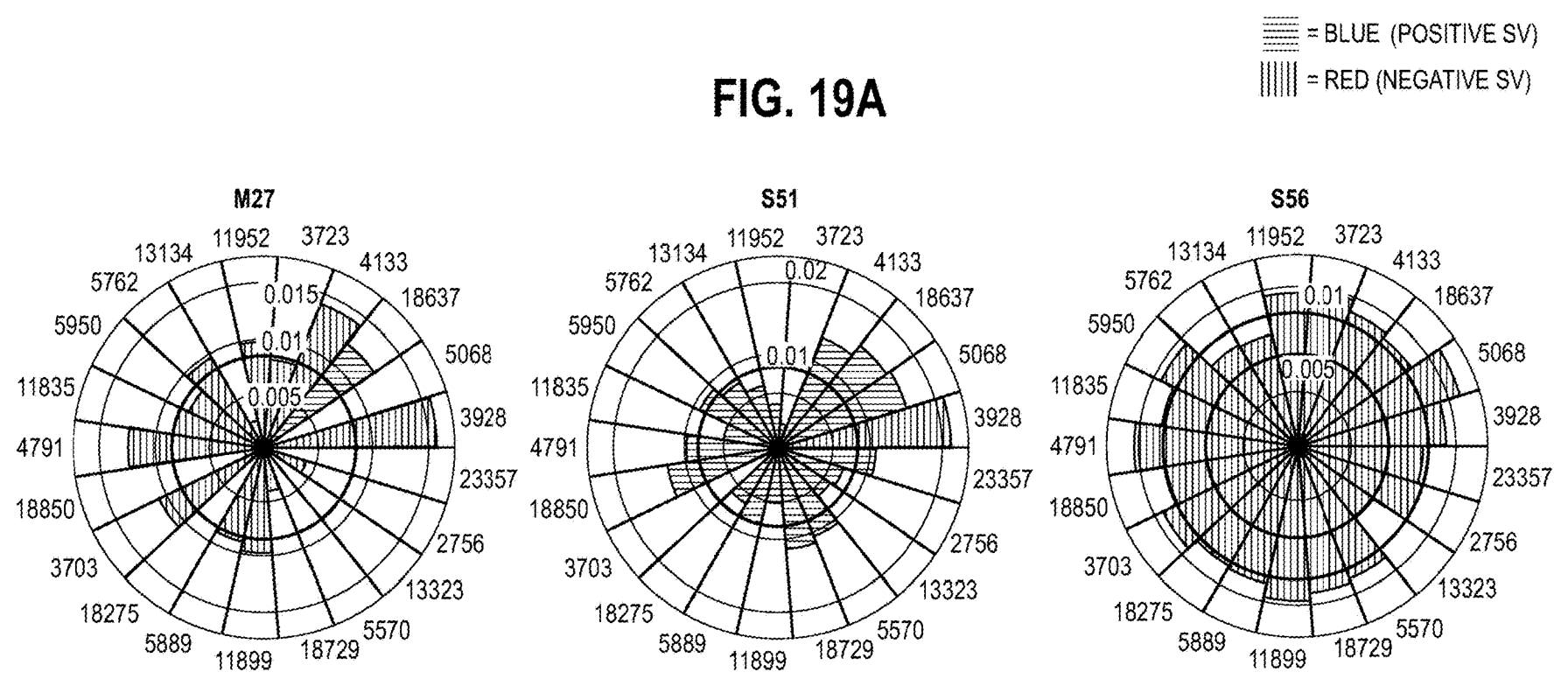

FIG. 19A shows radar plots of Shapley values for three representative samples from the sample set referred to in FIG. 18 with the BDX008 classifier. The 21 SVs with the greatest variance across the cohort are shown. Radial extent of each sector corresponds to magnitude of Shapley value, and coloring corresponds to sign (blue is positive Shapley value, red is negative Shapley value). The black ring is at radius 1/|M|. Shapley values were estimated using 5M Monte-Carlo subsets. A plot of the type shown in FIG. 19A could be incorporated into a report provided to a physician along with a test prediction in accordance with the BDX008 test.

Figure 19B:
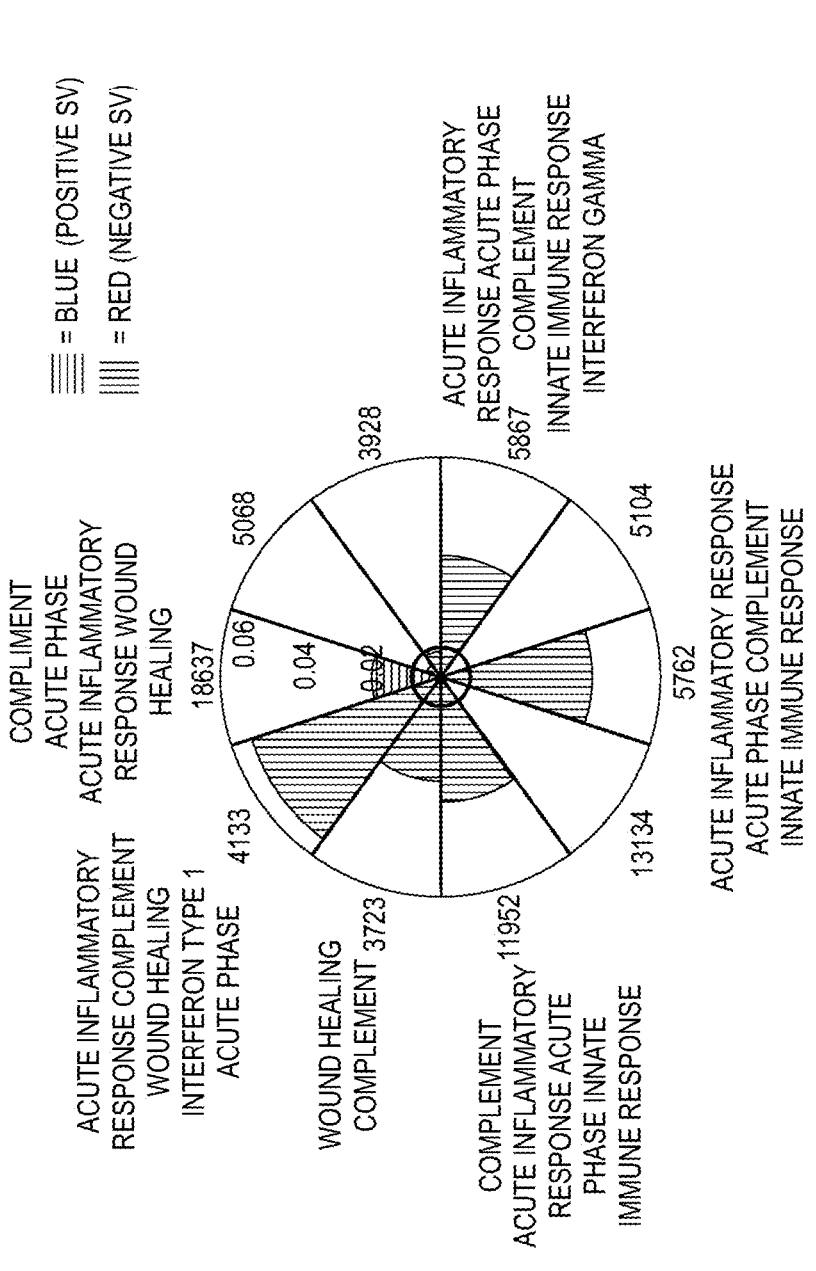

FIG. 19B is a radar plot of Shapley values for a sample from the sample set referred to in FIG. 18 with the BDX008 classifier. The 10 SVs with the greatest variance across the cohort are shown. Radial extent of each sector corresponds to magnitude of Shapley value, and coloring corresponds to sign (blue is positive Shapley value, red is negative Shapley value). The black ring is at radius 1/|M|. Shapley values were estimated using 5M Monte-Carlo subsets. The biological associations of the mass spectral features (calculated protein set enrichment analysis, see e.g., U.S. Pat. No. 10,007,766 and literature cited therein for details) for which the Shapley value exceeds 1/|M| are added to the plot. A plot of the type shown in FIG. 19A or 19B could be incorporated into a report provided to a physician along with a test prediction in accordance with the BDX008 test to provide the biological rationale behind the test prediction.

Figure 20:
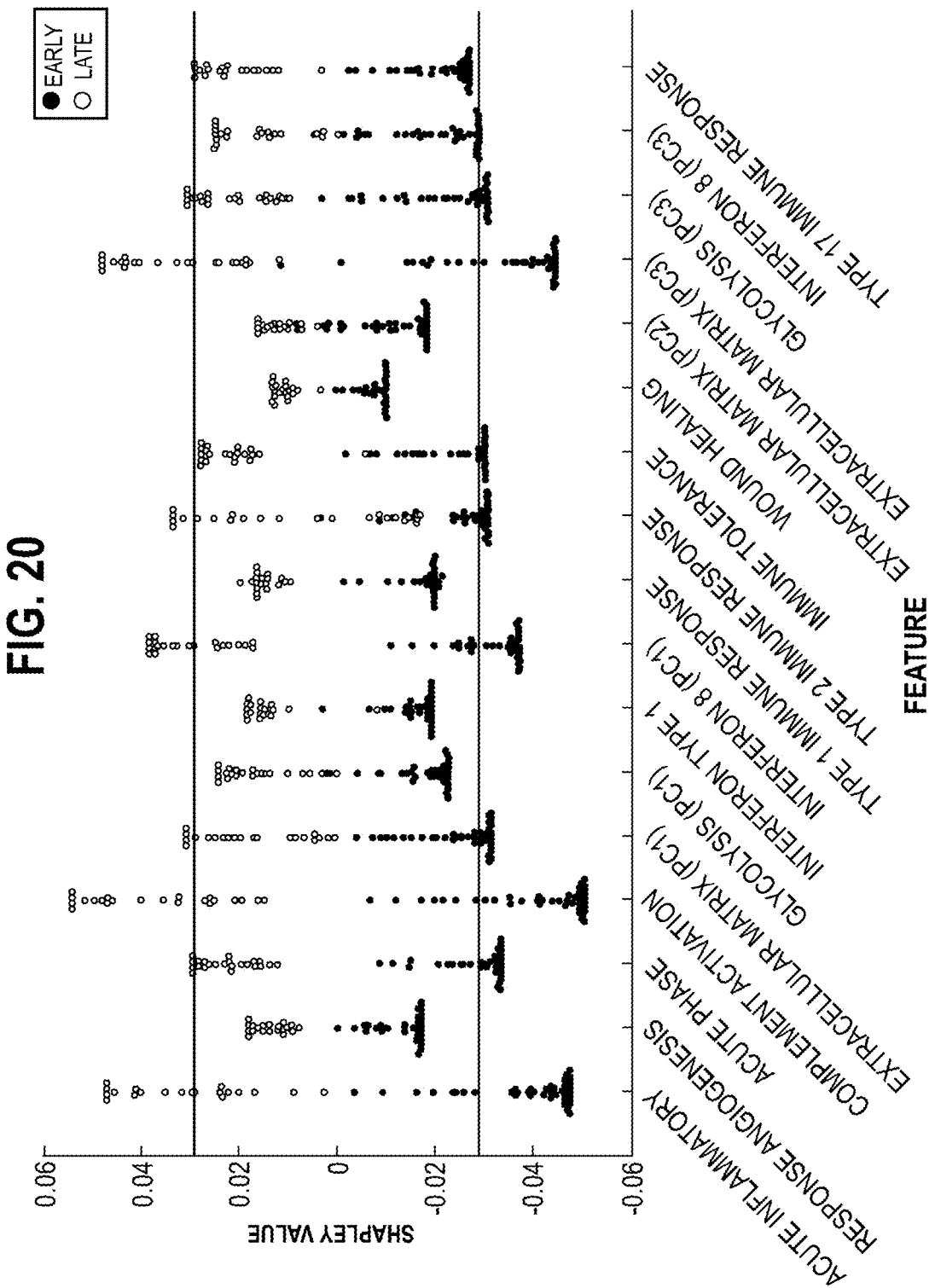

FIG. 20 is a Violin plot for a PSEA (Protein Set Enrichment Analysis) score test applied to test samples, illustrating an example of the present methods to calculating Shapley values for PSEA score tests. The PSEA score test was developed in accordance with the Diagnostic Cortex architecture. Shapley values were estimated using 1M Monte Carlo subsets.

DETAILED DESCRIPTION

I. Overview

Modern measurement techniques in the fields of proteomics, genomics, transcriptomics, and metabolomics generate large numbers of attributes (features) for each patient. Modern ML approaches provide clinically useful tests by utilizing the information in these highly multiplexed datasets to make effective and robust predictions of patient outcome. However, it is often unclear how these complex ML algorithms arrive at a prediction for a specific patient. This information would be helpful in physician-patient interactions.

In contrast to traditional biomarker approaches, where a test result is related to the amount of one or a small set of specific biochemical entities, based on some hypothesis of the biological relevance of these entities, in modern ML models there is no direct connection between disease specific biology and a test result. Indeed, it is one of the strengths of modern ML that it does not require a specific biological model or mechanistic hypothesis for making clinically meaningful predictions. If we could find out how the many attributes in a ML model are used, we might, in turn, learn something about the biological reasons behind a prediction for a particular patient. Further, if we could detect similar patterns of attribute usage within groups of patients, we would be able to use our ML model as a 'biomarker microscope' defining different disease phenotypes, i.e., as a tool for biomarker discovery characterized by our specific ML model.

The task, then, is to generate a measure of relative feature importance for a specified ML model for a specific sample, in contrast to feature importance measures, which assess the importance of features in representative sample sets in a model agnostic fashion. As explained in the Background section, viewing ML models as cooperative games with the features as players leads to the notion of SVs describing the relative feature importance for the prediction of a sample. Hence, in this disclosure we provide methods for interpreting a prediction as to a patient generated by a machine learning model in the form of a trained classifier, or hierarchy of trained classifiers which are combined using simple logical operations.

FIG. 1 is a high level description of a computer processing system 10 which implements a trained ML classifier 12 to generate a prediction 14 in accordance with a diagnostic test for a patient and calculates Shapley values providing explainability to the prediction in accordance with the present disclosure. A set of attributes or features 16 associated with the patient (PT) is obtained for example in the manner shown in FIG. 2, stored in memory and then supplied to the trained classifier 12. This set of attributes could, for example, be mass spectrometry data obtained from a blood or other biological sample, data obtained from an electronic health records, genomic or proteomic data, or combination thereof. The trained classifier (or hierarchical combination of classifiers) 12 is generated in accordance with the procedure described in U.S. Pat. No. 9,477,906, and in the publications of Röder et al., *A Dropout-Regularized Classifier Development Approach Optimized for Precision*

*Medicine Test Discovery from Omics Data*, BMC Bioinformatics. 2019; 20:325 and Röder et al., *Robust Identification of Molecular Phenotypes using Semi-Supervised Learning*, BMC Bioinformatics. 2019; 20:273. This will be described later in conjunction with FIG. 4. The classifier 12 is trained from a development set of samples and generates a prediction based on the set of attributes 16. The nature of the prediction will correspond to the clinical question the classifier 12 is developed on, such as "is the patient at high risk of developing an unfavorable outcome while hospitalized?", "is this patient at risk of early recurrence of cancer after surgery?", "is this patient likely to benefit from anti-PD-1 targeting drugs in treatment of melanoma or non-small cell lung cancer?" and so forth.

After the classifier generates the prediction, and using the set of attributes and the details of the trained classifier 12, a module 18 in the computer system is invoked which calculates the SVs for the attributes in the set 16, making use of the calculations and explanations provided in the following section, and see FIGS. 3B-3D. These calculations may take the form of performing many (e.g., a million or more) Monte Carlo samplings of subsets of features in the set 16. This sampling may also take into consideration Diagnostic Cortex classification when the sample is described with less features than in model training. It is important to note that we make use of the specific structure of the Diagnostic Cortex architecture to avoid the need for retraining of the classifier.

The SV calculation module 18 generates results shown at 20, which can be in graphical or text form, basically providing the calculated SVs for specific features in some human-understandable form, such as radar plots, Violin plots, a simple table, narrative format, or otherwise. The test result (prediction 14 and the SV results 20) are then combined into a report shown at 22 which combines the prediction, SVs, and optional commentary on the prediction and/or SVs in a convenient form for use by a physician and/or patient. Examples of reports are shown in FIGS. 9-11 discussed below.

FIG. 2 is an illustration of several possible physical process steps which could be used to generate the set of features (or "attributes") which are used for classification in accordance with the system of FIG. 1. For example, a blood sample 30 presented on a suitable medium 32 is introduced into a mass spectrometer (M/S) 34 which generates data in the form of integrated intensity values at specific m/Z ranges as is conventional in the art and described in the prior patent literature of Biodesix, Inc. This set of data is shown at 36. One preferred method for acquiring mass spectrometry data is the "deep MALDI" method described in U.S. Pat. No. 9,279,798, the content of which is incorporated by reference herein. Alternatively, the patient's electronic health record 38, containing basic patient characteristics (age, sex, race, smoker status, etc.), clinical data and laboratory data is accessed and specific parameters which are used by the classifier of FIG. 1 are extracted to form a set of attributes 40. As another example, the patient's sample 30 is provided to an instrument performing a genomic or proteomic assay 42, for example gene or protein expression levels, and the resulting data set is shown at 44. It will be noted in the example of mass spectrometry data, further processing of the data could be performed, such as Protein Set Enrichment Analysis (not shown). Basically, in this method a correlation is discovered between each mass spectral feature with biological functions. The method is described at length in the prior patents of Biodesix, see e.g., U.S. Pat. No. 10,007,766, and therefore a detailed description is omitted for the sake of brevity.

Figure 3A:
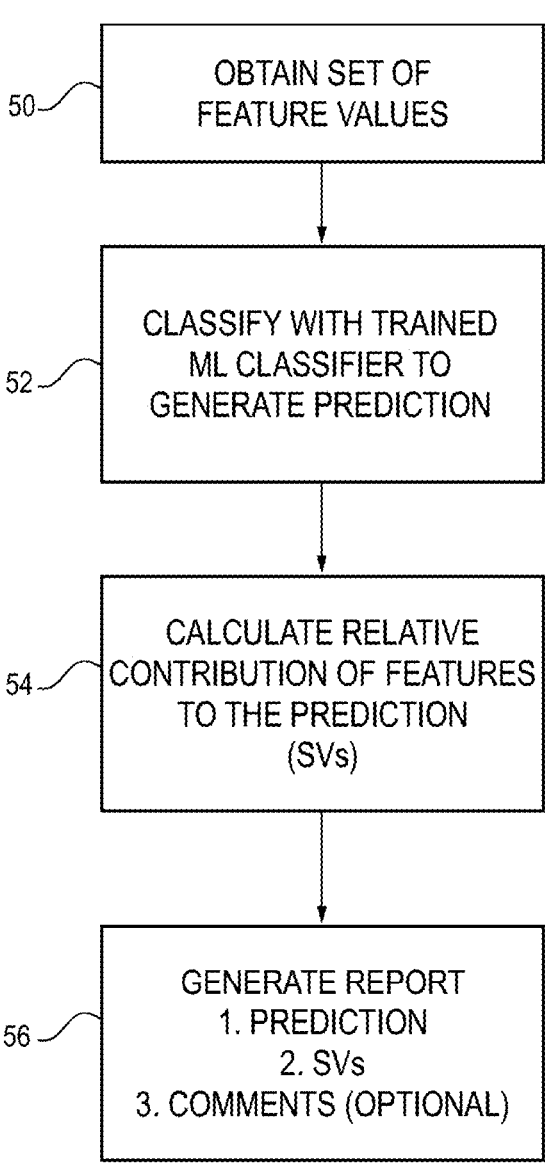
FIG. 3A is a flow chart showing one implementation of the method for generating a classification using the trained machine learning model of FIG. 1 and the Shapley values.
Figure 3B:
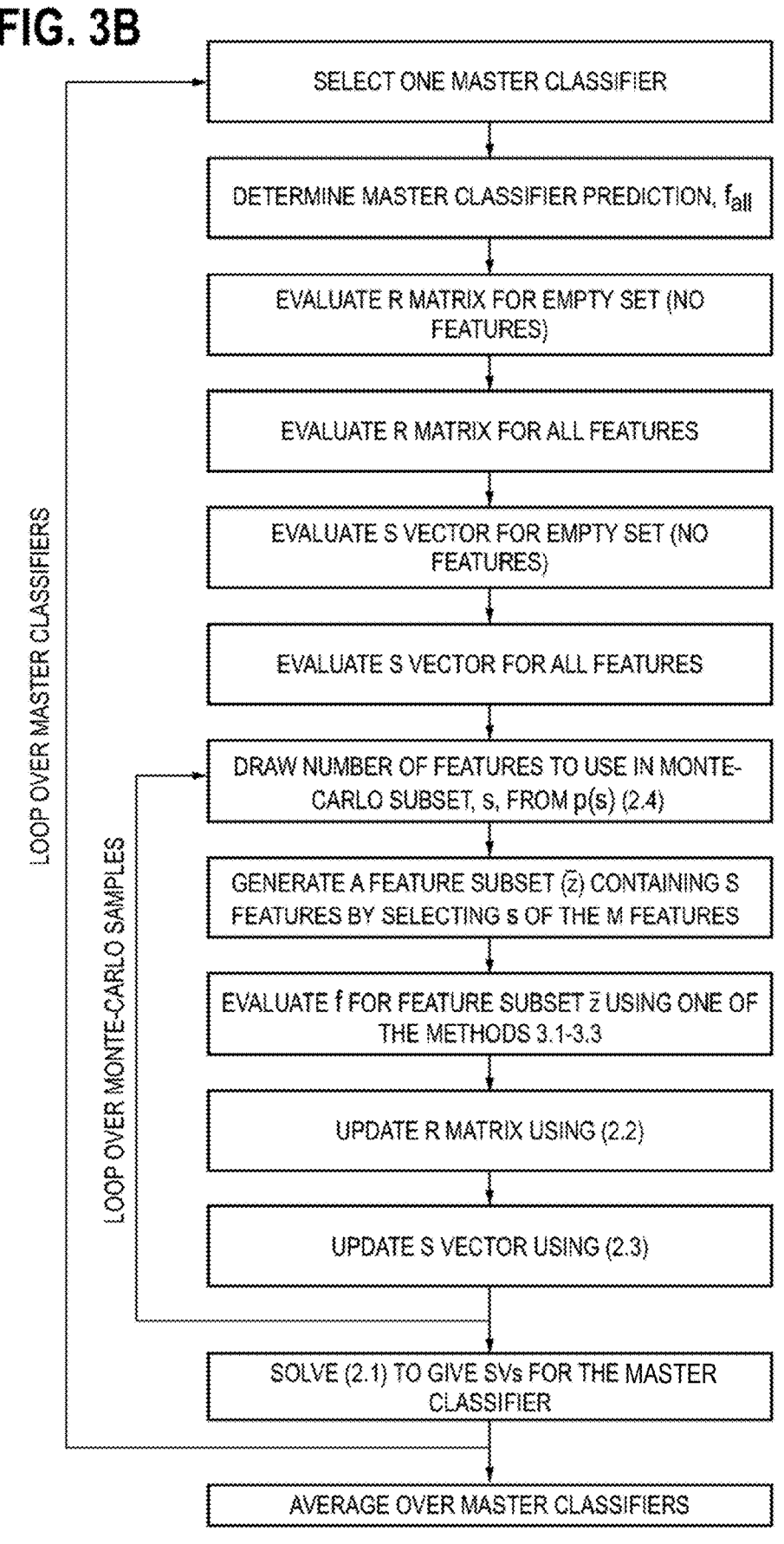
FIG. 3B is a flow chart showing how Shapley values are evaluated using the least squares method with Monte-Carlo sampling (section 2.1).
Figure 3D:
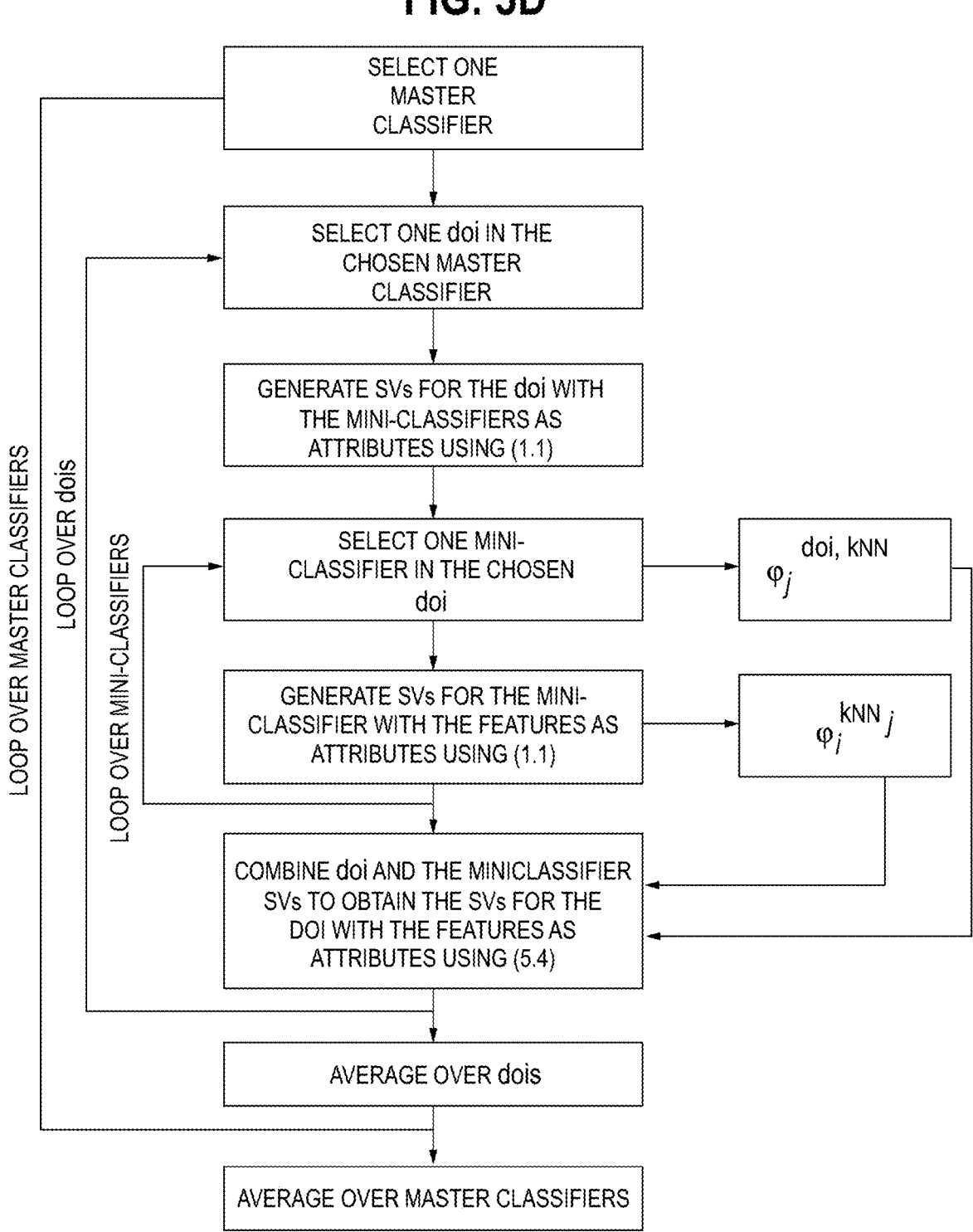
FIG. 3D is a flow chart showing how exact Shapley values are evaluated using the hierarchical approach (section 5.2).

FIG. 3 is a flow chart showing one implementation of the method for generating a classification using the trained classifier of FIG. 1 and the Shapley values. This procedure assumes the training and validation of the classifier from a development set of samples has already taken place. At step 50, we obtain the set of features values (or attributes) from the patient, either from their electronic record, from a physical process or measurement (see FIG. 2) or some combination thereof depending on how the classifier is designed and the attributes it uses to generate classification labels.

At step 52, we then classify the set obtained at step 50 with the trained classifier (see FIG. 1) and generate a prediction, e.g., "high risk", etc. for the patient.

At step 54, we calculate the relative contribution of each of the features obtained at step 50 to the prediction. In practice, this means calculation of the SVs as described in the following sections III and V.

At step 56, we then generate a report, containing (1) the prediction generated at step 52, the SVs generated at step 54, and optionally (and preferably) some comments on the prediction and/or the SVs to aid in understanding the prediction. Examples are shown in FIGS. 9-11 and will be described subsequently.

II. Diagnostic Cortex Architecture

Our ability to calculate SVs for classifiers which can be used in proteomics, genomics, transcriptomics, and metabolomics which use large numbers of attributes (features) is possible because of the certain inherent features and aspects of the design of the Diagnostic Cortex methodology of developing a classifier.

Figure 4:
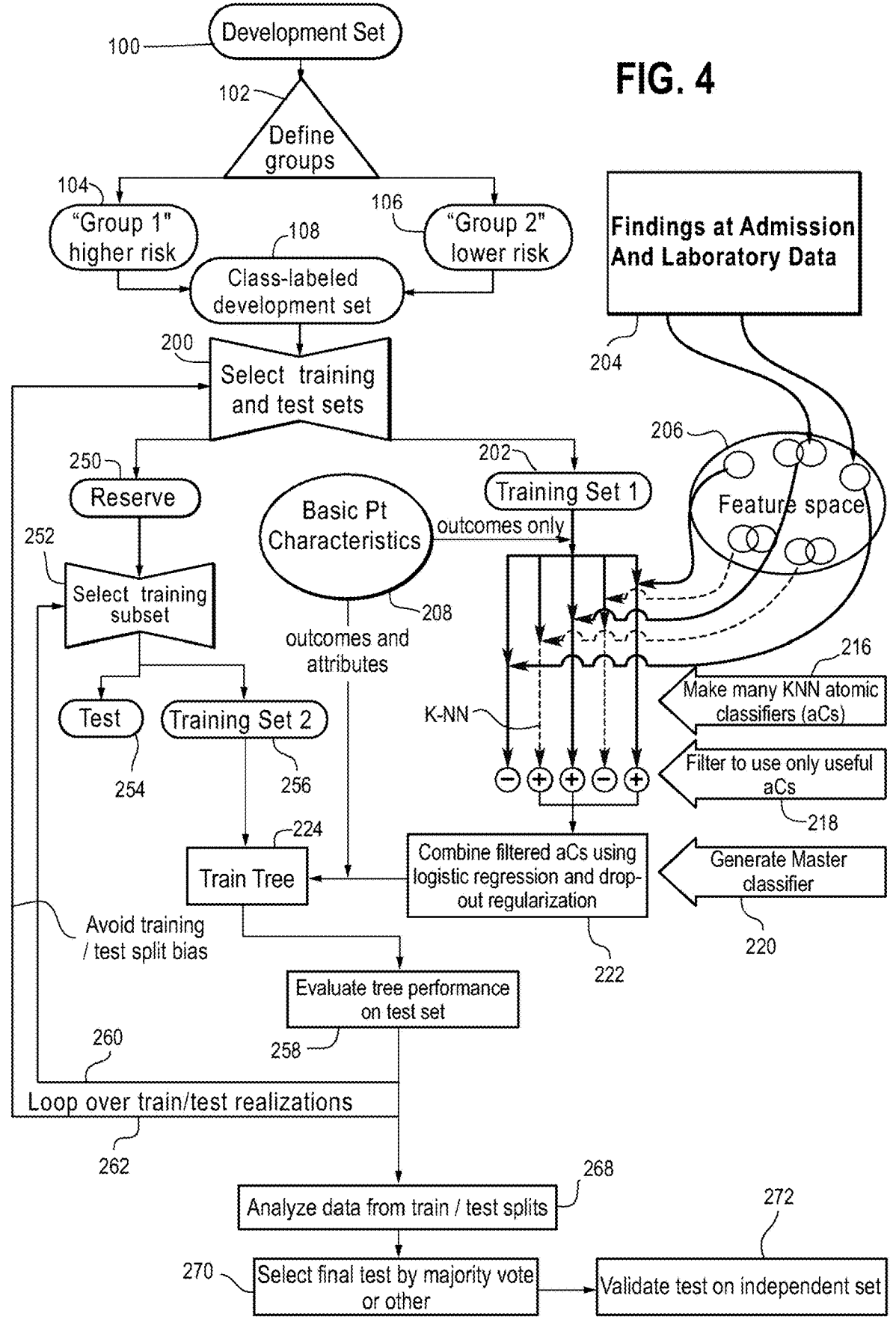
FIG. 4 is an illustration of a classifier development process which makes use of the Diagnostic Cortex architecture (generally shown in the right hand side of the figure) and a trained decision tree architecture (generally shown on the left hand side of the figure). We used this combined classifier development architecture to generate a test for prediction of risk of unfavorable outcomes for COVID-19 hospitalized patients based on a set of attributes including findings at admission, laboratory data, and basic patient characteristics. However, the architecture could be used to generate different tests, and the Diagnostic Cortex architecture could be used alone (without the trained decision trees) as demonstrated in numerous prior patents of the Assignee, e.g., U.S. Pat. No. 10,007,766. Furthermore, a test could be configured as a hierarchical combination of classifiers, each of which is generated by the methodology of FIG. 4 as a whole or, alternatively the Diagnostic Cortex architecture of FIG. 4, right hand side.

In particular, FIG. 4 is an illustration of a classifier development process which makes use of the Diagnostic Cortex architecture (generally shown in the right-hand side of the figure) and optionally a trained decision tree architecture (generally shown on the left-hand side of the figure). We used this combined classifier development architecture to generate a test for prediction of risk of unfavorable outcomes for COVID-19 hospitalized patients based on a set of attributes including findings at admission, laboratory data, and basic patient characteristics. However, the architecture could be used to generate different tests, and the Diagnostic Cortex architecture could be used alone (without the trained decision trees found on the left hand side of the Figure) as demonstrated in numerous prior patents of the Assignee, e.g., U.S. Pat. No. 10,007,766. Furthermore, a test could be configured as a hierarchical combination of classifiers, each of which is generated by the methodology of FIG. 4 or, alternatively the Diagnostic Cortex architecture of the right-hand side of FIG. 4.

Referring in particular to the procedure of FIG. 4, a development set for classifier training and generation is shown at 100 and can take the form of a multitude of patient samples, each having many attributes. Examples are given in the prior patent literature of Biodesix, and in the prior provisional application Ser. No. 63/125,527 filed on Dec. 15, 2020 for the COVID-19 hospitalized patient tests. See also U.S. patent application Ser. No. 17/344,352 filed Jun. 10, 2021, the content of which is incorporated by reference herein. The details are not pertinent to the present discussion since the methods of this document are generally applicable to different types of samples, attributes, and development sets.

At step 102 we define two classes, a "group 1" or higher risk class and a "group 2" or lower risk class, based on (human) inspection of the outcome data for the members of the development set. Based on such inspection we assign the class labels to the members of the development set resulting in a class-labeled development set 108. At step 200 we select a training subset, which splits the class labeled development set 108 into a reserve set 250 and a "training set 1" 202. The training set 1 202 is then subject to the combination of atomic classifiers with drop-out regularization training procedure explained in the prior patent and articles of Röder et al. cited above. Specifically, at step 216 we create many k-nearest neighbor (k-NN) atomic or mini-classifiers (all individual features, all possible combinations of pairs of features, and all possible combinations of triplets of features in the feature space). At step 218 have an optional filtering step to only retain those mini-classifiers that pass certain performance criteria. This step may or may not be performed, for example in the COVID-19 test development we did not filter out any of the k-NN mini-classifiers. At step 220, we then generate what we have called a "master classifier" by combining all of the mini-classifiers using logistic regression and drop-out regularization.

In step 216, as noted we construct a multitude of individual mini-classifiers using sets of feature values from the development set up to a pre-selected feature set size s (s=integer 1 . . . p). For example, a multiple of individual mini- (or "atomic") classifiers could be constructed using a single feature (s=1), or pairs of features (s=2), or three of the features (s=3), or even higher order combinations containing more than 3 features. The selection of a value of s will normally be small enough to allow the code implementing the method (and calculation of SVs using Monte Carlo simulations) to run in a reasonable amount of time, but could be larger in some circumstances or where longer code run-times are acceptable. The selection of a value of s also may be dictated by the number of measured variables (p) in the data set, and where p is in the hundreds, thousands or even tens of thousands, s will typically be 1, or 2 or possibly 3, depending on the computing resources available, and was 3 in the COVID-19 work. The mini-classifiers of step 216 execute a supervised learning classification algorithm, such as k-nearest neighbors (k-NN), in which the values for a feature, pairs or triplets of features of a sample instance are compared to the values of the same feature or features in a training set and the nearest neighbors (e.g., k=11) in an s-dimensional feature space are identified and by majority vote a class label is assigned to the sample instance for each mini-classifier. In practice, there may be thousands of such mini-classifiers depending on the number of features which are used for classification.

As noted, there is an optional filtering step 218. If this step is performed, we test the performance, for example the accuracy, of each of the individual mini-classifiers to correctly classify the sample, or measure the individual mini-classifier performance by some other metric (e.g. the Hazard Ratios (HRs) obtained between groups defined by the classifications of the individual mini-classifier for the training set samples) and retain only those mini-classifiers whose classification accuracy, predictive power, or other performance metric, exceeds a pre-defined threshold to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained in the filtering step 218. Alternative supervised classification algorithms could be used, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible k-NN classifiers using feature sets up to a maximum pre-selected size (parameter s). This gives us many "mini-classifiers": e.g. if we start with 100 features for each sample/patient (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step we only use those "mini-classifiers" that pass predefined criteria. These filtering criteria are chosen dependent on the particular problem: If one has a two-class classification problem, one would select only those mini-classifiers whose classification accuracy exceeds a pre-defined threshold, i.e., are predictive to some reasonable degree. Even with this filtering of "mini-classifiers" we end up with many thousands of "mini-classifier" candidates with performance spanning the whole range from borderline to decent to excellent performance.

In the COVID-19 work we discovered the filtering of the mini-classifiers did not substantially affect performance and therefore in the following discussion of step 220 all mini-classifiers constructed in step 216 were used in the logistic regression and drop-out regularization, and a filtering step 218 was not performed.

The method continues with step 220 of generating a Master Classifier (MC) indicated at 222 by combining the mini-classifiers using a regularized combination method. In one embodiment, this regularized combination method takes the form of repeatedly conducting a logistic training of the set of mini-classifiers to the class labels for the samples. This is done by randomly selecting a small fraction of the mini-classifiers as a result of carrying out an extreme dropout from the set of mini-classifiers (a technique referred to as drop-out regularization herein), and conducting logistic training on such selected mini-classifiers. While similar in spirit to standard classifier combination methods (see e.g. S. Tulyakov et al., *Review of Classifier Combination Methods*, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating mini-classifiers, we generate many logistic training steps by randomly selecting only a small fraction of the mini-classifiers for each of these logistic training steps. This is a regularization of the problem in the spirit of dropout as used in deep learning theory. In this case, where we have many mini-classifiers and a small training set, we use extreme dropout, where in excess of 99% of filtered mini-classifiers are dropped out in each iteration.

In more detail, the result of each mini-classifier is one of two values, either "Group1" or "Group2" in this example. We can then combine the results of the mini-classifiers by defining the probability P of obtaining a "Group1" label via standard logistic regression (see e.g. http://en.wikipedia.org/wiki/Logistic_regression:

$$P("Group1"|\text{feature values}) = \frac{\exp\left(\sum_{\text{mini-classifiers}} w_{mc}/(mc(\text{feature values}))\right)}{\text{Normalization}} \quad \text{Eq. (1)}$$

where I(mc(feature values))=1, if the mini-classifier mc applied to the feature values of a sample returns "Group2", and 0 if the mini-classifier returns "Group1". The weights $w_{mc}$ for the mini-classifiers are unknown and need to be determined from a regression fit of the above formula for all samples in the training set using +1 for the left hand side of the formula for the Group2-labeled samples in the training set, and 0 for the Group1-labeled samples, respectively.

As we have many more mini-classifiers, and therefore weights, than members of the training set, typically thousands of mini-classifiers and only tens of members, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same time, we use only a few of the mini-classifiers for a regression, but repeat this process many times in generating the master classifier. For example, we randomly pick three of the mini-classifiers, perform a regression for their three weights, pick another set of three mini-classifiers, and determine their weights, and repeat this process many times, generating many random picks, i.e. realizations of three mini-classifiers. The Master Classifier (222, FIG. 4) is then defined as the average of all the dropout realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

In one embodiment this above process (steps 200, 216, 218, 220 and 222) is performed for many different realizations of the separation of the development set into training and test sets and the resulting master classifiers are combined, in an ensemble manner, to form a final classifier, as described in the prior patent literature of Biodesix, such as U.S. Pat. No. 9,477,906.

Optional Combination of Diagnostic Cortex Classifier with Trained Decision Trees In the design of FIG. 4, we combine the master classifier generated at step 220 with a trained decision tree classifiers generated in the left hand side of FIG. 4, see 224. In particular, the classification output of the logistic regression and drop-out regularization 222 is then supplied along with basic patient characteristics to classification trees 224 which are trained separately in the procedure of the left hand-side of FIG. 4.

In particular, referring again to FIG. 4, the training subset selected at step 200 is split in training set 1 202 (and subject to the procedures explained above) and a reserve set 250. The reserve set is further sampled (30 times for the COVID-19 project) into a set 256 for training (Training Set 2) and a set for evaluation (Test Set 254). The training set 2 (256) is used to train a set of random classification tree classifiers 224, which includes the classification output of the Master Classifier 222 for samples in Training Set 2 and basic patient characteristics 208. Samples in the evaluation Test Set 254 are not used at all in training and can be used to generate out-of-bag classifications in an evaluation step 258. This process of selecting training subsets and splitting into test and training set 2 subsets is performed many times as represented by the inner loop 260, such as 30 times in the COVID-19 example. Furthermore, the procedure of training the classification trees 224 and generating master classifiers 222 is performed for many different training/test split realizations as indicated by the outer loop 262, for example 625 times in the COVID-19 example.

At step 268 we analyze the classification performance data from the many different training and test splits (step 200 and iterations through loop 262) and at step 270 we select a final test or implementation of the classifier, for example as a majority vote of all the 30×625 trained classification trees trained at step 224, by selecting one specific train/test split iteration that has optimum performance and generalizes well, or in some other manner. As indicated at 272, the classifier as configured and defined at step 270 is then validated on an independent sample set.

Referring to FIG. 4, in each sampling of the reserved set 250, a classification tree was grown on Training Set 2 (256) and the test set (254) was evaluated with it. The data was split at step 200 into ⅓ for Training Set 1 (202), ⅔ for Reserve set (250), and then equal proportions of the subsequent splits (252) of the Reserve set (250) to Training Set 2 (256) and the Test set (254).

The procedure for growing the classification trees (224) for the COVID-19 project was as follows:

1. For non-categorical features, the values of each feature were sampled to get a list of feature values to consider when splitting each node in the tree. The values were taken to be the $10^{th}$, $20^{th}$, . . . , $90^{th}$ percentile of observed feature values in the training set.

2. The training set 2 (256) was recursively split: The entire training set 2 (256) was assigned to the initial node. The procedure for each recursive node split was as follows:

a. Sample the features in the training set 2 (256): Take a random subset of floor(sqrt(<number of features>)) features out of the list of the total set of features in the training data.

b. If the depth of the tree exceeds 100: stop this recursion.

c. For each possible value of the feature, for each feature in this feature subset, split the samples at this node by feature value into two candidate children nodes. If both groups have at least one sample present, consider this split valid. Calculate and store the weighted change in cross entropy from the parent node to the candidate children nodes. The class entropy for a set of samples with some classes is defined in terms of the class proportions in the set, $p_i$, as: $I_C = -\Sigma_{i \in classes} p_i * \log(p_i)$, with $0*\log(0)$ taken to be the limit from the right which is 0. The average entropy gain from the parent to the child nodes with the left node containing fraction $f_{left}$ of the samples and the right node containing fraction $f_{right}$ is: $L_C = I_C$ (parent)$-(f_{left} * I_C(\text{left}) + f_{right} * I_C(\text{right}))$.

d. If no possible splits are found, stop this recursion.

e. Pick the feature and associated feature value that gives the largest change in cross entropy as defined in (c).

f. Assign each group the label (event or no event) corresponding to the majority of its members.

g. Split one child node.

h. Split the other child node.

The trained classification trees 224 now play the role of the logistic regression master classifiers in the original "Diagnostic Cortex" procedure for the purpose of obtaining the final (binary) class label for a new sample, e.g., Group1 (higher risk) or Group 2 (lower risk). Out of bag estimates are obtained by looking at the prediction of each classification tree for which a sample was in the test set. For the purpose of generating Receiver Operator Characteristic (ROC) curves, a binary classifier needs a continuous score that can be thresholded to produce classifications for different choices of the threshold. For the classifiers that did not include additional decision trees, the output probability or logit from the master classifier logistic regression step in each bag was used as this score. For a given threshold, master classifiers giving a score of less than the threshold were treated as voting for higher risk and the modified majority vote was then done as normal to get the final classification. For the models with additional classification trees, this score was taken to be the fraction of trees voting for higher risk. For the COVID-19 project, a majority vote was used as the selection of the final test in step 270 that could be applied to patients from an independent test set or other unseen patients. (This was implemented as an out-of-bag estimate to obtain classifications for patients in the development set.)

III. Methods of Calculating SVs Using Monte Carlo Sampling of Subsets of M Attributes/Features With the above description in mind, we will now explain in greater detail the logic and mathematics for calculations of the SVs for classifiers developed in accordance with the Diagnostic Cortex procedure of U.S. Pat. No. 9,477,906, Röder et al., *A Dropout-Regularized Classifier Development Approach Optimized for Precision Medicine Test Discovery from Omics Data*, BMC Bioinformatics. 2019; 20:325 and Röder et al., *Robust Identification of Molecular Phenotypes using Semi-Supervised Learning*, BMC Bioinformatics. 2019; 20:273, as exemplified by the methodology shown in the right-hand side of FIG. 4, specifically steps 216, 218, 220 and 222 described above.

It will be appreciated that the calculations and logic described below will be embodied in program instructions in a suitable language such as MATLAB and implemented in the computer system 10 of FIG. 1. A person skilled in the art will be able to generate such instructions from the descriptions which follow, and from the flow charts of FIGS. 3B-3D.

1. Formulations of SV 1.1. Original formulation for the Shapley value of a feature j specific to a sample, $\varphi_j$.

$$\varphi_j = \sum_{s \in S \backslash \{j\}} \frac{1}{M \binom{M-1}{|s|}} (f(s \cup \{j\}) - f(s)) \qquad \text{Eq. 1.1}$$

where S is the powerset (i.e., set of all subsets) of M features, and f is the value of a test (classification) for a given sample. Shapley values are normalized such that $$\sum_{j=1}^{M} \varphi_j = f_{all} - f_0,$$

where $f_{all}$ is the classification for the sample using all features and $f_0$ is the classification of the empty set.

1.2. Least squares formulation for all Shapley values $\hat{\varphi}_{SV} = (\varphi_0, \ldots, \varphi_M)$ $$\hat{\varphi}_{SV} = \underset{\varphi \in \mathcal{R}^{|M|}}{\text{argmin}} \left\| \sqrt{W} (\hat{Z}\varphi - \hat{f}) \right\|_2^2 \qquad \text{Eq. 1.2}$$

W is the Shapley kernel defined below in section 2.2, $\hat{Z}$ is a stacked matrix of subset descriptors (see section 2 below), $\hat{f}$ is a vector of test results for each possible subset. The minimization in (1.2) needs to be performed such that the sum of all Shapley values adds to the test classification of the sample and such that the test classification of the empty subset is a pre-specified value.

2. Monte-Carlo Sampling of Subsets.

If we want to directly use (1.1) or (1.2) to estimate Shapley values we need to evaluate $|S| = 2^M$ terms each of which requires a retraining of the classifier f on all subsets $s \in S$. In this section we will discuss two approaches that perform importance weighted Monte-Carlo sampling of these subsets. For simpler notation we will represent a subset s of S as a binary number with M digits, where 1/0 represents the presence/absence of a feature in the subset, e.g. for M=4 features we have 16 feature subsets represented as 0000, 1000, 0100, 0010, 0001, 1100, 1010, 1001, 0110, 0101, 0011, 1110, 1101, 1011, 0111, 1111. We will denote the vectors of digits as $\bar{z}_i$, i=0, . . . , $2^M - 1$. In both methods presented below the calculation of Shapley values involves a weighted sum over elements of a set $\mathcal{F} = \{\bar{z}^1, \ldots, \bar{z}^{|\mathcal{F}|}\}$ of feature subsets, drawn from the powerset S using specified distributions. For exact Shapley values $\mathcal{F} = S$ and there is no weighting.

2.1 Here we describe subset sampling using the least squares formulation of Equation 1.2. We present a modification of an algorithm outlined in Brian D. Williamson and Jean Feng, *Efficient nonparametric statistical inference on population feature importance using Shapley values*, Proceedings of the 37$^{th}$ International Conference on Machine Learning, Online, PMLR 119, 2020, pp. 3-4. In this formulation the constrained minimization in (1.2) is performed using a vector of two Lagrange multipliers. The minimum in (1.2) can be shown to be the solution of $$\begin{bmatrix} 2\hat{Z}'\hat{W}\hat{Z} & \hat{G}' \\ \hat{G} & 0 \end{bmatrix} \begin{pmatrix} \bar{\varphi} \\ \bar{\lambda} \end{pmatrix} = \begin{pmatrix} 2\hat{Z}'\hat{W}\hat{f} \\ \bar{C} \end{pmatrix} \qquad \text{Eq. 2.1}$$

where $\hat{Z}$ is the stacked matrix of $\bar{z}_i$ vectors of size $|\mathcal{F}| \times (M+1)$ with the first column being a vector of all 1's. $\hat{W}$ is a diagonal matrix of size $|\mathcal{F}| \times |\mathcal{F}|$ with elements depending on the chosen sampling distribution $$\hat{G} = \begin{pmatrix} 1 & 0 & \ldots \\ 1 & 1 & \ldots \end{pmatrix}$$

is a 2×(M+1) matrix, and $$\bar{c} = \begin{pmatrix} f_0 \\ f_{all} \end{pmatrix}.$$

The Shapley values are in the vector $\bar{\varphi}'=(\varphi_0, \varphi_1, \ldots, \varphi_M)$ and $\bar{f}$ is the vector of predictions of subsets $\bar{z}_i$.

At a first glance this formulation may require the multiplication of large matrices. However, the products $R=\hat{Z}'\hat{W}$ $\hat{Z}$ and $S=\hat{Z}'\hat{W}\bar{f}$ are of size $(M+1)\times(M+1)$ and $(M+1)\times 1$, respectively. Enumerating the subsets by an index $L=1, \ldots, |\mathcal{F}|$ one can show that these products can be updated via (in components)

$$R_{kl}^{L+1} = R_{k,l}^{L} + \left(1, z_k^L\right)' W^{L+1,L+1}\left(1, z_k^L\right) \qquad \text{Eq. 2.2}$$

And $$S_k^{L+1} = S_k^L + \left(1, z_k^{L1}\right)' W^{L+1,L+1} f^{L+1} \qquad \text{Eq. 2.3}$$

where $f^L$ is the value of the test for the $L^{th}$ subset. In order to sample subsets $\bar{z}_i$ in an efficient manner, one can use the following procedure: First one draws the number of features in a configuration, s, from the distribution $$p(s) \sim \begin{pmatrix} M \\ s \end{pmatrix} / \begin{pmatrix} M-2 \\ s-1 \end{pmatrix}, \qquad \text{Eq. 2.4}$$

and then one randomly picks s features from M to get a subset. If Monte-Carlo subsets are drawn using this procedure, the matrices W are identity matrices. The process of Shapley values calculation using this method for a Diagnostic Cortex classifier is illustrated in FIG. 3B.

2.2 Another recent approach used in subset sampling is to evaluate all pairwise differences of Shapley values. These differences can be written as $$\varphi_i - \varphi_j = \frac{1}{M-1} \sum_{s \in S \setminus \{i,j\}} \frac{1}{\begin{pmatrix} M-2 \\ |s| \end{pmatrix}} (f(s \cup \{i\}) - f(s \cup \{j\})). \qquad \text{Eq. 2.5}$$

The paper of Jia R, Dao D, Wang B, Hubis F A, Hynes N, Gurel N M, et al. *Towards Efficient Data Valuation Based on the Shapley Value.* Proceedings of the 22nd International Conference on Artificial Intelligence and Statistics (AIS-TATS) 2019. PMLR: Volume 89, shows a clever way (Algorithm 1 in Jia et al.) to sample these differences using a specific sampling distribution function chosen to optimize convergence to the true answer with as few sampling subsets as possible using $(\varepsilon, \delta)$ formalism. The Jia et al. paper and Algorithm 1 thereof is incorporated by reference herein.

Subsets are drawn according to the number of features they contain, e.g. the configuration $\bar{z}_i=(1, 0, 0, 1, 1, 0)$ drawn from a set with 6 possible features which contains 3 features i.e. $|\bar{z}_i|=3$, from the distribution $$p(|z_i|) = \frac{1}{Q}\left(\frac{1}{|z_i|} + \frac{1}{M - |z_i|}\right) \qquad \text{Eq. 2.6}$$

where $$Q = 2\sum_{k=1}^{M-1} \frac{1}{k}.$$

So, to generate a subset one first draws the number of features $s=|\bar{z}_i|$, and then randomly distributes s1's on M places. If the number of Monte-Carlo subsamples is T, the T-approximation to the Shapley value differences can be obtained from $$(\varphi_i - \varphi_j)_T = \frac{Q}{T}\sum_{t=1}^{T} f(\bar{z}_t)(z_{t,i} - z_{t,j}) \qquad \text{Eq. 2.7}$$

where $z_{t,i}$ is the $i^{th}$ digit in the binary representation of the subset t.

Shapley values for a T-approximation are then shown to be the solution of the linear system:

$$\hat{Y}\bar{\varphi}=\bar{u}, \qquad \text{Eq. 2.8}$$

where the M×M matrix $\hat{Y}$ has $-1$'s on the diagonal apart from the (1, 1) element, which is 1, and where the first row and column have 1's, and other elements are 0, e.g. for M=3 $\hat{Y}=$ $$\begin{pmatrix} 1 & 1 & 1 \\ 1 & -1 & 0 \\ 1 & 0 & -1 \end{pmatrix}.$$

The right-hand side vector $\bar{u}=(f_{all}-f_0, (\varphi_1-\varphi_2)_T, \ldots, (\varphi_1-\varphi_M)_T)$. The process of Shapley values calculation using this method for a Diagnostic Cortex classifier is illustrated in FIG. 3C.

In practice, for large numbers of features, available CPU resources limit the number of subsets for which classifications can be generated. As the evaluation of the actual Shapley values from the differences requires the solution of a linear system of equations the error bounds can only be with respect to the $l_2$ norm for all M Shapley values, and do not provide error estimates for individual Shapley values.

Note: If the set of sampled subsets in either approach is equal to the powerset of M features either approach gives the exact Shapley values as expected. Thus, the methods permit the calculation of SVs either exactly or by approximation.

3. Diagnostic Cortex Classification with Missing Features

As we need to work with feature subsets, we need to define how to generate the value (classification) of a Diagnostic Cortex test applied to a specific sample when the sample is described with fewer features than in model training. It is important to note that we make use of the specific structure of the Diagnostic Cortex architecture to avoid retraining the classifier.

As explained above, the Diagnostic Cortex tests take ensemble averages over subtests, master classifiers, trained on different splits (bags) of the data into training and test sets. This averaging is simple, and we can decompose the classification of a sample into independent classifications for each master classifier. Hence, we can focus on how to construct the value of master classifier applied to a feature subset of a sample.

For illustration purposes we construct a very simple master classifier from 4 features, where we use only singles and pairs of features for the mini-classifiers, and where we use only 4 dois (drop-out iterations), leaving in 2 mini-classifiers (leave-in number=2) in each doi. FIG. 12 is an illustration of a Diagnostic Cortex master classifier constructed from 4 features indicated by the circles in the top row. All ten possible singles and pairs are input into respective mini-classifiers, kNN's, shown in boxes in the second row. Four drop-out iterations are shown in the bottom row, where $p(x, y)=(1/(1+\exp(-(\beta_0+\beta_1 x+\beta_2 y))))$ and the $\beta_i$ are the logistic regression coefficients generated in training.

The classification f of a master classifier is the average over all drop-out iterations $$f = \frac{1}{N_{doi}}\sum_{doi=1}^{N_{doi}} p^i,$$

where $p^i$ is the value of the logistic regression probability evaluated from the labels of the it's mini-classifiers applied to the sample. For the simple example from FIG. 1 we get $$f = \frac{1}{4}(p^1 + p^2 + p^3 + p^4).$$

In the following we discuss three options to evaluate f for feature subsets.

3.1 Dealing with Missing Features on the Drop-Out Iteration Level

Each drop-out iteration, doi, uses a set of features that are defined by the mini-classifiers in this doi. If one or many of these features are not in the subset for which we want to generate a classification, this doi does not contribute. Formally, for r being the set of features in the subset, and $m_{doi}$ being the set of features used in a doi, we can then write the value of a master classifier as:

$$f(r) = \frac{1}{\sum_{doi=1}^{N_{doi}} I^1(m_{doi}, r)}\sum_{doi=1}^{N_{doi}} I^1(m_{doi}, r)p^{doi} \qquad \text{Eq. 3.1}$$

where the indicator function $I^1$ is defined as $$I^1(m, r) = \begin{cases} 1 & \text{iff } m \in r \\ 0 & \text{otherwise} \end{cases} \qquad \text{Eq. 3.2}$$

As an example considering the subset r={$f_1$, $f_2$, $f_4$} for the simple Diagnostic Cortex master classifier depicted in FIG. 12 we obtain $$f = \frac{1}{2}(p^1 + p^2).$$

3.2 Dealing with Missing Features on the Mini-Classifier Level

Alternatively, but not as close to the spirit of Diagnostic Cortex classification as described in 3.1, we can replace the output of a mini-classifier by the uninformative value of ½, if a feature is missing for a mini-classifier (a kNN normally returns 0 or 1). Let $t_{i,doi}$ be the set of features used by the $i^{th}$ mini-classifier in drop-out iteration doi ($\in \{1, \ldots,$ leave-in number$\}$). Then we can write the value of a master classifier as:

$$f(r) = \frac{1}{N_{doi}}\sum_{doi=1}^{N_{doi}} p^{doi}(\bar{g}) \qquad \text{Eq. 3.3}$$

with the row vector $$\bar{g}(r, doi) = (I_1^2(r, doi), \ldots, I_{leave-in\ number}^2(r, doi)) \text{ and}$$

$$I_i^2(r, doi) = \begin{cases} kNN_i & \text{iff } t_{i,doi} \in r \\ 1/2 & \text{otherwise} \end{cases} \qquad \text{Eq. 3.4}$$

As an example, considering the subset r={$f_1$, $f_2$, $f_4$} for the simple master classifier depicted in 3.2, we obtain $$f = \frac{1}{4}$$

$$\Big(p^1(kNN(f_1), kNN(f_2)) +$$

$$p^2(kNN(f_1), kNN(f_1, f_2)) + p^3\Big(\frac{1}{2}, \frac{1}{2}\Big) + p^4\Big(kNN(f_2, f_4), \frac{1}{2}\Big)\Big).$$

3.3 Dealing with the Case where Many Dois Contain all Features

The number of features used in a doi is roughly equal to the leave-in number times the number of features used in the mini-classifiers. For example, for 30 features, i.e. |M|=30, for leave-in number=5 and going 6 deep in the mini-classifiers a doi uses on average of the order of 30 features. In this case Shapley values calculated using the approach from section (3.1) can still describe which features are pre-dominantly involved in a classification, but due to the size of the feature coalitions, detailed relative feature importance is washed out. Note that this behavior reflects the Diagnostic Cortex model most closely, as it more accurately describes the usage of features in the model.

If one is more interested in un-importance of features and willing to pay the price that the resulting Shapley values are somewhat less related to the detailed workings of the model, the approach described in section (3.2) provides more granularity for less important features. For even closer resemblance on the feature level one can further drill down even deeper into the model hierarchy and modify the mini-classifiers for missing features by reducing the arguments in a particular mini-classifier if that feature is absent. This leads to:

$$f(r) = \frac{1}{N_{doi}}\sum_{doi=1}^{N_{doi}} p^{doi}(\bar{h}) \qquad \text{Eq. 3.5}$$

with the row vector $$\bar{h}(r, doi) = \left(I_1^3(r, doi), \; ... \; , I_{leave\text{-}in\,number}^3(r, doi)\right) \text{ and}$$

$$I_i^3(r, doi) = \begin{cases} kNN_i & \text{iff } t_{i,doi} \in r \\ kNN(t_{i,doi}) & \text{iff } 0 < t_{i,doi} \cap r < |t_{i,doi}| \\ 1/2 & \text{otherwise} \end{cases} \qquad \text{Eq. 3.6}$$

where $kNN(t_{i,doi})$ is the 'retrained' kNN using features $t_{i,doi}$. As an example, considering the subset $r=\{f_1, f_2, f_4\}$ for the simple Diagnostic Cortex master classifier depicted in FIG. 12, we obtain $$f = \frac{1}{4}$$

$$\left( p^1(kNN(f_1), kNN(f_2)) + p^2(kNN(f_1), kNN(f_1, f_2)) + \right.$$

$$\left. p^3\left(\frac{1}{2}, kNN(f_2)\right) + p^4(kNN(f_2, f_4), kNN(f_4)) \right)$$

IV. Examples of Monte Carlo Sampling of SVs

The Monte-Carlo sampling approach using Shapley value differences described in section 2.2 and the missing feature procedure described in 3.1 was implemented in C# in a custom software package to take advantage of parallelization on our high-performance compute cluster.

Classifications as a function of subset configuration are generated using the high-performance implementation for each Diagnostic Cortex master classifier and for each sample. These classifications per bag are averaged over all master classifiers, and Shapley values are then the solution of the linear system (2.6) for each sample.

There are different types of Diagnostic Cortex tests depending on whether the continuous values coming from the individual master classifiers are converted into a binary label by thresholding using a cut-off of 0.5 or not before performing the ensemble average. We denote the un-thresholded values as average-p and the thresholded values as classification. In the following we will show results only for average-p.

Example 1: Shapley Values for COVID-19 Hospitalization Outcome Risk Prediction As explained above in conjunction with FIG. 4, we developed a set of tests for COVID-19 hospitalized patients and specifically tests for predicting risk of certain unfavorable outcomes, including development of ARDS, intubation, transfer to the ICU. These tests, and the development set we used to generate the tests, are described in our prior provisional application and in U.S. Ser. No. 17/344,352 filed Jun. 10, 2021 and a detailed description will be omitted for the sake of brevity. The tests were constructed as a hierarchical arrangement of classifiers, namely an initial binary classifier that stratified the patients into high and low risk groups, and subsidiary or child classifiers that further stratified the high and low risk groups into lowest risk, highest risk and intermediate risk groups. What is pertinent, at least for present purposes, is that, using the methods described in the previous section, we were able to calculate SVs for the Diagnostic Cortex portions of the risk assessment classifiers, see FIG. 4, right hand side. The remaining parts of the risk assessment classifiers were ensemble averages of trees constructed using only a very small number of attributes, see the description of FIG. 4, left hand side. The small number of attributes allowed an exact SV calculation over the exponential number of terms in the sum, with model retraining for each attribute subset.

SVs were evaluated for each of the classifiers used in each of the risk assessment tests for 50 patients from the validation cohort. Patients were selected so that there was somewhat equal representation across all possible test risk groups and endpoints. Race and gender were also considered in the selection, but representative populations across these attributes was secondary to risk group and endpoint.

FIGS. 6, 7 and 8 show Shapley values for each patient and feature for each individual classifier that make up the hierarchical tests. Shapley values that are negative correspond to a classification of higher risk (higher risk classification corresponds to −1 and lower risk classification corresponds to +1), and larger magnitude implies a greater contribution from that attribute. Patients are grouped by the risk classification of each classifier and the hierarchical structure that gives the final risk label for each test is shown. A reference line is drawn at ±1/(number of attributes) which corresponds to the Shapley Values obtained when all features contribute equally to classification.

The tree component of the first split (initial binary) classifiers was treated separately from the Diagnostic Cortex component. As described above, the Diagnostic Cortex lends itself quite well to a Monte-Carlo sampling method for evaluating SVs. The trees did not fit into this schema. However, these trees only use 5 attributes: the output classification label from the Diagnostic Cortex, race, age, gender, and weight. This small number of attributes allows for exact computation of SVs by retraining the trees for all possible subsets of included features. The result is a SV for each of the five attributes, including the Diagnostic Cortex output label. A large magnitude SV for this label is interpretable as a large contribution from the attributes that were used in the Diagnostic Cortex training to the assignment of risk for that classifier. The SVs for the first Diagnostic Cortex models are given in parallel to those of the trees.

In reading FIG. 6 showing the Shapley values for the test predicting risk of developing ARDS, some broad conclusions can be drawn. For example, we see that the Diagnostic Cortex attribute in the trees plays a significant role in assigning both higher and lower risk classifications in the initial binary classifier. Gender does not seem to play a role at all, and race, age, and weight play a significant role for some patients. Looking at corresponding Diagnostic Cortex SVs, we see that LDH, CRP, and BUN (i.e., laboratory data findings as part of the feature space 204 in FIG. 4, Lactate Dehydrogenase, C-Reactive Protein, and Blood Urea Nitrogen, respectively) all frequently contribute to a higher risk classification while CRP and D-dimer frequently contribute to a lower risk classification, in addition to several other attributes to a lesser extent. For patients that are classified as low risk by the initial binary classifier, the low risk child classifier diagram shows CRP and D-dimer contributing significantly again to a lower risk classification.

From this, we could conclude that for many patients that get a lowest risk final classification, CRP and D-dimer contributed substantially, with race and age also contributing a fair amount for some patients. Focusing on the highest risk group, the high risk child classifier shows LDH and oxygen saturation contributing to high risk classification of many patients. So, for a final test label of highest risk, LDH, CRP, BUN, and oxygen saturation substantially contribute.

These observations indicate that the calculation of SVs can be useful not only to generate reports for physicians explaining model predictions, but also in classifier development itself, and lead to further insights into the biological foundation of the test classifications, and can be used to guide patient treatment.

Figure 5:
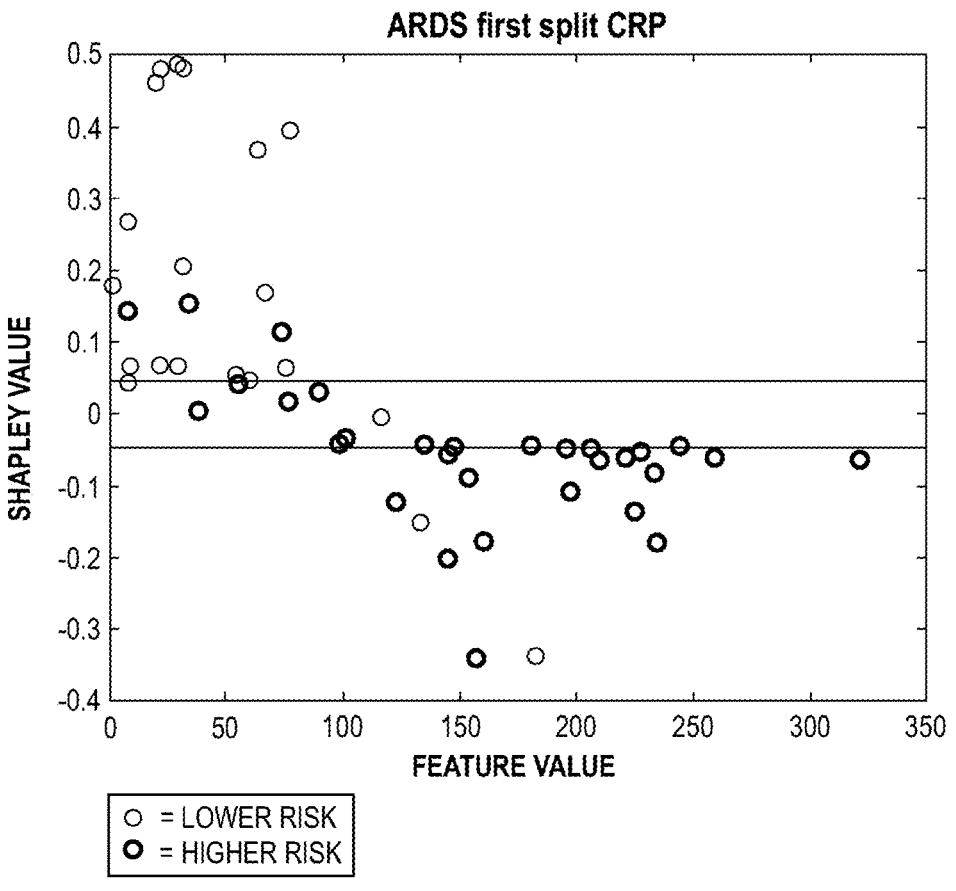
FIG. 5 is an illustration of one possible manner in which calculated SVs can also be plotted in graphical form.

SVs can also be plotted simultaneously with attribute values. FIG. 5 shows a scatter plot of SV and CRP value coded by corresponding classification. We see that generally lower values of CRP correspond to lower risk of developing ARDS in COVID-19 hospitalized patients.

SVs for the test predicting risk of admission to the ICU are shown in FIG. 7. Again, the Diagnostic Cortex component contributes heavily for assigning both lower and higher risk with weight contributing to a higher risk classification for some patients and race contributing to a lower risk classification for some patients. Gender plays more of a role but is still not as pronounced as the other attributes. The Diagnostic Cortex component of the initial binary classifier shows LDH and CRP playing the largest role in assigning a higher risk classification, but several other features contribute as well. Many attributes contribute to a lower risk classification with ferritin, CRP, D-dimer, LDH, and platelet count seemingly playing more of a role than heart rate, respiratory rate, oxygen saturation and WBC. The low risk child classifier shows CRP and D-dimer contributing to a lower risk classification, so for a final risk label of lowest risk, CRP and D-dimer are perhaps the most important, and ferritin, LDH, platelet count, heart rate, respiratory rate, oxygen saturation, and WBC also contribute. The high risk child classifier shows oxygen saturation, respiratory rate, LDH, CRP, and ferritin contributing to a higher risk classification, so LDH and D-dimer are perhaps the most important with oxygen saturation, respiratory rate, CRP, ferritin, and weight also contributing.

SVs for the test predicting the risk of intubation are shown in FIG. 8. Again, the Diagnostic Cortex component contributes heavily for assigning both lower and higher risk, with race and age also contributing to a lower risk classification for some patients. The Diagnostic Cortex SVs show LDH, CRP and BUN contributing to a higher risk classification and CRP, D-dimer, LDH, and BUN contributing to a lower risk classification. The low risk child classifier shows CRP contributing to a lower risk classification; so, for a final classification of lowest risk, CRP is likely the most important, with D-dimer, LDH, BUN, race, and age also contributing. The high risk child classifier shows oxygen saturation and LDH contributing to a higher risk classification, so LDH seems to be the most important contributor for a classification of highest risk with oxygen saturation, CRP, and BUN also contributing.

Overall, we see that each of the tests is producing a classification based on a complex interplay of multiple attributes and that, while we can discern some general trends across the cohort, the relative importance of the attributes to classification is dependent on the patient.

The preceding observations consider how the attributes affected the classification of samples in aggregate. These observations were fairly general; we believe the information at the patient level is more directly interpretable and can be very informative for assisting physicians and patients in understanding or being steered towards personalized treatment options. FIGS. 9 through 11 show three examples of how results might be presented to physicians/patients in the form of a report for an individual prediction using, as an example the COVID-19 test predicting risk of intubation. Interpretations (optional) are given in the comments. In each of the individual diagrams, the SVs are given in a graphical format (Radar plot) with a reference line at 1/(number of features). Color indicates higher (red) or lower (green) risk in the case of the initial binary (first split) classifier and final classification level: highest, high, low, or lowest (red, orange, yellow, or green) for the child classifiers. The SVs could be reported in other formats, such as for example, in table format, or as plain text in narrative format.

It will be appreciated that the form of the report is not particularly important and can change from the format shown in FIGS. 9-11.

Example 2: Evaluation of Shapley Values on Synthetic Data

To gain a better understanding of the dependence of the Shapley value calculation using Monte-Carlo sampling, we investigated Shapley values for synthetic data, in which we control the feature distribution of the data.

Description of the Synthetic Data Models

Synthetic data were generated from a multivariate normal distribution. Half of all features (lower numbered features) were uninformative and uncorrelated with phenotype. The remaining half (higher numbered features) were correlated with phenotype, with a mean feature value difference of p between phenotypes. Informative feature values were randomly correlated, uncorrelated, or perfectly correlated with each other. Equal numbers of samples of each phenotype (group) were generated and separated into a development set for training a Diagnostic Cortex test and a test set for evaluation of Shapley values. The training set size was typically 60/40 for early/late phenotypes, respectively.

Tests were generated using the label-flip algorithm (see US patent application publication no. 2021/0118538 for a description of the procedure) trained on OS with Hazard ratio filtering with a cut-off of 1.7. OS data for a sample were generated from an exponential distribution and matched to the phenotype using principal components of their feature values. Shapley values were calculated by dealing with missing features at the doi level (section 3.1) using the Monte-Carlo sampling approach in 2.2.

Results and Description of Graphs

Convergence of Shapley values per sample and feature: The convergence of Shapley values as a function of number of Monte-Carlo subsets sampled can be directly evaluated. Often one is interested in the ranking of Shapley values. In a graphical description we rank the Shapley values by their absolute value.

Convergence of Shapley values per sample: We can trace the changes in ranks averaged over all features for each sample as a function of number of Monte-Carlo subset samples. Specifically, we define the average change in ranks for a sample between one number of Monte-Carlo subsets and the next number of Monte-Carlo subsets as the average over all features of the absolute value of the difference in ranks for each feature between the greater and smaller number of Monte Carlos subsets and we plot this as a function of the greater Monte-Carlos subset number.

Distribution of Shapley values for a sample set: Violin plots show the distribution of Shapley values for each feature. Each dot represents a sample colored by classification (Early as blue and Late as gold). Reference lines are plotted at the Shapley value that would be expected if all features contributed equally to the classification. This value is ±1/M.

Dependence on Number of Features

To study the convergence of the Monte-Carlo algorithm we generated Diagnostic Cortex tests with different numbers of features. In FIG. 2 of Appendix C of our prior provisional application Ser. No. 63/125,527 we show the summary rank convergence for different numbers of features. We observe that convergence depends strongly on the number of features and becomes slower for larger number of features. The convergence for different samples is similar.

Dependence on Number of Drop Out Iterations (Dois)

An important number in Diagnostic Cortex models is the number of drop-out iterations. We observe that changing the number of drop-out iterations from 10,000 (FIG. 13) to 100,000 (FIG. 14) does not change the Shapley values much at all. This is expected if the predictions do not change very much for the two numbers of drop-out iterations. We note that even with 100,00 dois we still only sparsely sample the possible combinations of mini-classifiers that we could select for each doi. The Shapley values of un-informative features are all smaller than the value 1/M expected when all features were to contribute equally and the predictions were close to ±1.

Dependence of Shapley Values on Feature Correlations

As Shapley values are obtained from all possible feature subsets, they reflect the correlations between features. To investigate the role of feature correlations in how Diagnostic Cortex tests use features we compare Diagnostic Cortex tests developed on synthetic data with zero, random, and perfect feature correlation.

For un-informative features there is little difference in Shapley values between no correlation (FIG. 15) and random correlations (FIG. 16). FIG. 15 is a Violin plot of Shapley values for a validation set of 20 samples (10 per phenotype) for a synthetic data model. Development and validation sets consisted of 50 features (25 uninformative uncorrelated, 25 informative with μ=5 uncorrelated). 120 samples (60 per phenotype) were used in the development set, number of dois=10,000, and leave-in number=10 averaging over 315 master classifiers. Shapley values were estimated with 1M Monte-Carlo subsets using the method of 2.2 for sampling and the method of 3.1 for predictions for missing features. FIG. 16 is a Violin plot of Shapley values for a validation set of 20 samples (10 per phenotype) for a synthetic data model. Development and validation sets consisted of 50 features (25 uninformative uncorrelated, 25 informative with μ=5 randomly correlated). 120 samples (60 per phenotype) were used in the development set, number of dois=10,000, and leave-in number=10 averaging over 315 master classifiers. Shapley values were estimated with 1M Monte-Carlo subsets using the method of 2.2 for sampling and the method of 3.1 for predictions for missing features. Even non-informative features have a finite, non-zero value, reflecting the coalition structure of the Diagnostic Cortex arrangement (uninformative features are paired with informative ones in the mini-classifiers and dois and theoretically uninformative features may have some utility for classification in the given development set).

The relative importance of informative features can vary depending on correlation, exact feature values in the training set and the doi sampling of the mini-classifiers, see e.g. the relative importance of features 49 and 50 in FIGS. 15 and 16.

FIG. 17 is Violin plot of Shapley values for a validation set of 20 samples (10 per phenotype) for a synthetic data model. Development and validation sets consisted of 50 features (25 uninformative uncorrelated, 25 informative with μ=5 perfectly correlated). 120 samples (60 per phenotype) were used for development, number of dois=10,000, and leave-in number=10 averaging over 315 master classifiers. Shapley values were estimated with 1M Monte-Carlo subsets using the method of 2.2 for sampling and the method of 3.1 for predictions for missing features. In the case of perfect correlations, we would expect all Shapley values for informative features to have the same value. The observed variations in informative features' Shapley values in FIG. 17 are smaller than for the no correlation (FIG. 15) and random correlation case (FIG. 16). The remaining non-uniformity reflects the incomplete sampling of features over dois, and we expect this would become smaller if we were to increase the number of dois, i.e. by better sampling of the feature space of the dois.

Summarizing, we have shown that Shapley values do reflect feature correlations. This is important because in approximations to Shapley values (like SHAP or kernelShap) feature correlations are at best incompletely handled and sometimes ignored leading to possibly misleading results for relative feature importance.

Example 3: Shapley Values for Molecular Diagnostic Test—Predict Outcome in Ovarian Cancer To explore the feasibility of generating Shapley values for a real clinical test we used a test developed to predict outcome after surgery from pre-surgery samples in ovarian cancer. The test, which uses 269 features obtained from mass spectrometry of a blood-based sample, and its development are described in Kasimir-Bauer S, Roder J, Obermayr E, et al. *Definition and Independent Validation of a Proteomic-Classifier in Ovarian Cancer*. Cancers (Basel). 2020; 12(9): 2519. We evaluated Shapley values for two samples, A and B, not in the development cohort using 2M Monte-Carlo subsets.

The two samples, A and B, show quite different convergence behavior, with Shapley values for sample A converging more slowly than those for sample B (FIG. 5A of Appendix C of our prior provisional application). Inspecting the convergence of Shapley values for individual features (FIG. 5B for A and FIG. 5C for B, again from Appendix C of our prior provisional application) we see Shapley values show less dependence on subset number in sample B than in sample A especially for Shapley values with largest magnitude. In fact in sample B, the Shapley values for the top 4 features (m/z peaks at 11733, 23130, 8821, 13326) and the bottom 5 features (10162, 28134, 7995, 5864, 11443) appear not to change much beyond 1M Monte-Carlo subsets, whereas there are no similarly stable SVs for sample A. If we relax the condition of numerical stability and just care about ranks, we could tentatively identify features (18631,4211, 8821,11733) as the top ranked SVs in sample A from FIG. 5d of appendix C of our prior provisional.

In summary, while it appears possible to identify a set of most important features for this test with 2M Monte-Carlo subsets, for a clinical application one would need to increase the number of used subsets substantially to generate reliable radar plots (see e.g. the section on representing Shapley values in the description of the COVID-19 risk assessment tests above).

Example 4: Shapley Values for Molecular
Diagnostic Test—Predict Cancer Patient Benefit of
Anti-PD-1 Targeting Drugs Another example where we applied our Shapley value
Monte-Carlo method to a clinical test is the test referred to
as "BDX008" described in Example 1 of U.S. Pat. No.
10,007,766, and referred to in that document as "IS2", the
description of which is incorporated by reference. The
BDX008 test was developed using Deep MALDI spectral
data generated from pretreatment serum samples collected
from a cohort of 119 patients with advanced melanoma
treated with nivolumab with or without a peptide vaccine
(NCT01176461). Mass spectral data were used within the
Diagnostic Cortex platform with iterative refinement of
training class definition and classifier (label flip approach).
Bagged feature deselection was used to remove features
showing little or no ability to classify samples into better and
worse outcome groups at each iterative refinement step. The
final BDX008 test used 59 mass spectral features for classification. Details on the development and performance of
the test can be found in Ascierto et al., *Proteomic test for
anti-PD-1 checkpoint blockade treatment of metastatic
melanoma with and without BRAF mutations*, J Immunother
Cancer. 2019; 7: 91. BDX008 was developed using the
approach of weight averaging across the regularizing drop-
out iterations. i.e., within each training/test split, many
(10,000) subsets of 10 of the filtered mini-classifiers are
selected; this constitutes 10,000 dropout iterations. Each doi
subset is combined using the training set with logistic
regression. The logistic regression weight for each used
mini-classifier is stored for each doi. The final weight for a
specific mini-classifier is the average of the weights obtained
for each classifier across the dois, and the final output for
each training/test split is a logistic regression including all
mini-classifiers, combined with these averaged weights.

Shapley values cannot be calculated for Diagnostic Cor-
tex classifiers created using weight averaging using the
methods in this document. Hence, BDX008 was recreated,
as closely as possible, using the probability averaging
approach. In this case, the weights for each mini-classifier in
each doi are all stored. The final output for each training/test
split is an average over all dropout iteration probabilities,
with each individual doi evaluated using the mini-classifier
weights from training that doi. This redevelopment was
achieved by taking the input feature-deselected feature table
of the final flip of the original BDX008 test with its training
class label definitions and running the Diagnostic Cortex
procedure with probability averaging without iterative
refinement (i.e., no flips). All parameters were kept the same
as for the original BDX008 test. All 119 samples used in test
development received the same out-of-bag classification as
for the original BDX008 test.

Shapley value evaluation for samples used in the devel-
opment of a test may be unreliable. Hence, pretreatment
samples from an independent cohort of patients with
advanced melanoma treated with anti-PD-1 agents was used
for BDX008 SV assessment. This was the patient cohort
studied in the above-cited Ascierto et al. paper.

Shapley values were estimated using 5M Monte-Carlo
subsets. The overall convergence is summarized in FIG. 6*a*
of Appendix C of our prior provisional application. Overall
convergence was good, but as in example 3 there are
differences between samples. To further check on the con-
vergence of Shapley values, we looked at the convergence
for the best and worst converging samples from FIG. 6*a*, i.e.
sample M27 for the best convergence (FIG. 6C of Appendix B) and sample M13 for the worst (FIG. 6B of Appendix C).
Almost all Shapley values look stable in M27, and, while
there is some variation in M13, changes beyond 3M Monte-
Carlo subsets are mainly between neighboring features
(sorted by Shapley value). The distribution of Shapley
values for the whole Ascierto set is shown in the violin plot
of FIG. 18 of this document. As expected, the features used
by BDX008 to arrive at a phenotype label early or late differ
by sample. Still, there are some features that stick out, e.g.
features 5068 and 18637 are more important for a Late
phenotype.

One can represent the Shapley values for a sample as a
radar plot (see FIGS. 19A and 19B of this document), giving
for an individual sample a more detailed representation of
how BDX008 arrived at a classification, which might pro-
vide a physician or a researcher with helpful information.
For sample M27, left side of FIG. 19A, which was classified
as poor prognosis (early), the most relevant features are
3928, 4133 and 4791 all contributing to the early classifi-
cation whereas feature 18637 is relevant but counter to the
classification. This competition between features is even
more pronounced for sample S51, center of FIG. 19A, a
good prognosis (late) sample, where the most important
feature 3928 is antagonistic to the sample classification.
Sample S56, right side of FIG. 19A, provides an example
where all features contribute fairly evenly to the classifica-
tion label of poor prognosis (early). In the radar plots of FIG.
19, the 21 SVs with the most variance across the cohort are
shown. Radial extent of each sector corresponds to magni-
tude of Shapley value, and coloring corresponds to sign
(blue is positive Shapley value, red is negative Shapley
value). The black ring is at radius 1/M. Shapley values were
estimated using 5M Monte-Carlo subsets. Further, FIG. 19B
shows how the utility of the radar plot presentation of the
test results and Shapley values could be enhanced by the
addition of information on the biological significance of the
features found to be most important for determining the test
result (i.e., those with the highest magnitude Shapley val-
ues). It has been demonstrated that the amplitude of mass
spectral features can be associated with levels of biological
processes (see the explanation in U.S. Pat. No. 10,007,766
and J. Grigorieva et al., *Application of protein set enrich-
ment analysis to correlation of protein functional sets with
mass spectral features and multivariate proteomic tests*.
Clinical Mass Spectrometry 15:44-53 (2020)). Hence, one
can identify biological processes associated with the mass
spectral features shown to be most important in the deter-
mination of the test results of an individual patient, via their
large amplitude Shapley values, and provide these associ-
ated biological processes to the physician and patient. This
may help with acceptance of the test by providing a more
direct connection between a test result and the underlying
biology and could help personalize treatment plan decisions
for the patient.

Example 5: Shapley Values for PSEA Score Tests

Seventeen protein set enrichment analysis (PSEA) bio-
logical process scores (for details on this technique, see
Roder et al., Clinical Mass Spectrometry. 8 (2020) 13:26 and
U.S. Pat. No. 10,007,766) were generated from the Deep
MALDI mass spectra acquired from pretreatment serum
from 118 patients with advanced melanoma treated with
nivolumab with or without a peptide vaccine
(NCT01176461). The 17 scores for each sample were used
as features within the Diagnostic Cortex platform using
iterative refinement of training class definitions (label flips)

to create a classifier stratifying patients into two groups with better and worse outcomes. The classifier used 9-nearest neighbor mini-classifiers constructed with up to 3 of the scores at once, combining these mini-classifiers in 5,000 dropout iterations each including 10 mini-classifiers.

SV evaluation for samples used in the development of a test may be unreliable. Hence, pretreatment samples from an independent cohort of patients with advanced melanoma treated with anti-PD-1 agents was used for SV assessment. This was the patient cohort studied in Ascierto et al. paper cited previously.

An inspection of the summary convergence plots showed that the Shapley values for all samples were well converged using 1M Monte-Carlo subsets as the number of features, 17, is relatively small.

From the violin plot of Shapley values (FIG. 20) one can see that complement activation, acute inflammatory response, interferon γ, and the third principal component of the extra-cellular matrix score are most influential in determining the late/early phenotype labels, and hence are associated with better or worse prognosis in this indication. Conversely, angiogenesis, glycolysis, type 1 immune response, interferon type 1, wound healing, and the second principal component of the extra-cellular matrix did not contribute substantially to the phenotype.

Again, for an individual patient, one could report these Shapley values, e.g. in the form of a report including the prediction and a radar plot, optionally with commentary or observations, to inform a physician on the contributing factors related to good and poor prognostic phenotypes.

V. Exact Shapley Values from Diagnostic Cortex Tests

For the approach described in section 3.2 of Part III to deal with missing features on the mini-classifier rather than the doi level, we can derive a formulation for Diagnostic Cortex Shapley values that leads to substantial computational speed-up, enabling the full summation over all subsets, leading to exact calculation of Shapley Values and not merely approximations from Monte-Carlo sampling as in the explanation of section III above and in the above examples.

For illustration on the master classifier level we start with the original Shapley value formula (1.1) and insert the explicit calculation for a Diagnostic Cortex master classifier (using 3.3).

$$\varphi_j = \sum_{s \in S \setminus \{j\}} \frac{1}{M\binom{M-1}{|s|}} (f(s \cup \{j\}) - f(s)) \qquad \text{Eq. 5.1}$$

$$= \sum_{s \in S \setminus \{j\}} \frac{1}{M\binom{M-1}{|s|}}$$

$$\left[ \frac{1}{N_{doi}} \sum_{doi=1}^{N_{doi}} \left( (p^{doi}(\overline{g}(s \cup \{j\}, doi)) - p^{doi}(\overline{g}(s, doi)) ) \right) \right]$$

Now we can reorder the sums in (5.1) and write it as an average over drop-out iterations.

$$\varphi_j = \frac{1}{N_{doi}} \sum_{doi=1}^{N_{doi}} \varphi_j^{doi} \qquad \text{Eq. 5.2}$$

where $$\varphi_j^{doi}$$

are the Shapley values for each doi defined by $$\varphi_j^{doi} = \sum_{s \in S \setminus \{j\}} \frac{1}{M\binom{M-1}{|s|}} \left( p^{doi}(\overline{g}(s \cup \{j\}, doi)) - p^{doi}(\overline{g}(s, doi)) \right) \qquad \text{Eq. 5.3}$$

Note that we can't do this with approach described in section 3.1, because the pre-factor in formula $$\frac{1}{\sum_{doi=1}^{N_{doi}} J^1(m_{doi}, r)}, \qquad (3.1)$$

depends on the subsets.

The sum over subsets in (5.3) runs over all $2^M$ subsets of the powerset of M features, but we know that each doi uses only $$N_{doi}^{firs} \left( N_{doi}^{firs} \le 2 * \text{leave-in number} \right)$$

features, and that the Shapley values for the features not in a drop-out iteration are identically zero for this doi (by the dummy axiom of Shapley values). Hence, we can calculate the Shapley values for a particular doi using only $$2^{N_{doi}^{firs}}$$

subsets.

The doi Shapley values in (5.3) can be calculated using the least-squares formalism (section 2.2), if one takes care of doi-local classification values for the empty set and full test classification value using equations (3.3) and (3.4). One advantage of using the least squares formalism is that one can pre-calculate the matrices R in (2.2) for all possible values of $$N_{doi}^{firs}$$

in the interval $[_{leave-in \ number}, 2*_{leave-in \ number}]$, as the R matrices do not depend on a sample's classification.

5.1 Comparison Between Exact Shapley Values for Two Ways of Handling Missing Features We used a synthetic data model where we could calculate exact Shapley values using a complete summation over all $2^{18}=262,144$ possible subsets. The training set of 30 samples per group was drawn from a multivariate normal distribution with 18 features. The first 9 features were uninformative, i.e. their group means were the same. The second 9 features were informative, having a difference of 1.5 between their group means and are randomly correlated. We trained a single Diagnostic Cortex master classifier with 300 drop-out iterations using 7NNs as mini-classifiers. We varied the leave-in number from 2 to 8, as we know from the discussion in section 3 that different ways of dealing with missing features affect the behavior as a function of leave-in number.

The results for the option of dealing with missing features on the doi level described in section 3.1 are summarized in FIG. 8_a_ of Appendix C of our prior provisional application and for the option of dealing with missing features on the mini-classifier level described in section 3.2 in FIG. 8_b_ of Appendix C of our prior provisional application.

As expected, when dealing with missing features on the doi level, Shapley values for uninformative features (U1-U9) are strongly leave-in number dependent but can be reasonably differentiated from informative features (I9-I18) for leave-in numbers less than 4. For larger leave-in numbers the contrast between informative and uninformative features is washed out as uninformative features increasingly appear only in coalition with informative features in the drop-out iterations. This behavior reflects how the model is using the features. For larger leave-in numbers the Diagnostic Cortex uses essentially all the features. For Diagnostic Cortex models with smaller leave-in numbers randomness in the sample configuration and the random selection of doi configurations are reflected in the Shapley values. We note that in the setting for which the Diagnostic Cortex was defined and in which it is used for real world datasets, we would be in the regime where each doi uses only a small fraction of the total number of available attributes. Hence, as long as the information in the many attributes is not extremely diluted (i.e. as long as there is a reasonable proportion of attributes containing some information for the desired classification task (informative features)), we should not observe dependence on the choice of leave-in numbers and we will be able to differentiate informative and non-informative features.

In contrast, for the option of dealing with missing features on the mini-classifier level there is a much weaker dependence of Shapley values on leave-in number. This very weak dependence of Shapley values on the model parameter leave-in number is an illustration that option 3.2 of dealing with missing features leads to Shapley values less reflective of respective details on how the model is using the features.

For typical Diagnostic Cortex tests, where the number of features vastly exceeds the number of features in a doi, we expect either option of dealing with missing features to give very similar answers.

5.2 Hierarchical Calculation of Exact SVs

A further increase in computational efficiency can be obtained using the hierarchical nature of each doi. We can decompose the SVs for a doi with features as attributes (players in the game) into SVs for a doi with mini-classifiers as attributes multiplied by SVs for mini-classifiers with features as attributes. We can calculate the SVs for mini-classifiers (which have a factor of ≈L fewer features) and the SVs for a doi with mini-classifiers as features directly from the SV definition (1.1). Formally, using this concept, we can write the SVs for the $i^{th}$ feature of a doi as $$\varphi_j^{doi} = \sum_{j=1}^{L} \varphi_j^{doi,kNN} \varphi_i^{kNN} \frac{1}{f_{all}^{kNN_j} - f_0^{kNN_j}},$$ Eq 5.4 where $$\varphi_j^{doi,kNN}$$

is the SV of a doi with mini-classifiers as players, $$\varphi_i^{kNN_j}$$

is the SV for the $i^{th}$ feature of the $j^{th}$ mini-classifier in a doi, and $$f_{all}^{kNN_j} \text{ and } f_0^{kNN_j}$$

are the predictions for the $j^{th}$ mini-classifier using all features and the empty set, respectively. The process of evaluation of Shapley values for Diagnostic Cortex classifiers using this hierarchical approach is illustrated in the flow chart of FIG. 3D.

VI Practical Uses

As will now be appreciated from the above description, there are many practical uses to the calculation of Shapley vales in clinical diagnostic tests. For one, they provide model explainability, which gives confidence in the model predictions and aids in adoption of the model and its predictions in a clinical setting. Further, by comparison of SVs across a multitude of patients one can detect similar patterns of attribute usage within groups of patients, accordingly one can use the model and associated SVs as a 'biomarker microscope' defining different disease phenotypes, i.e., as a tool for biomarker discovery characterized by our specific ML model. In a clinical setting one could provide a customer with these Shapley values in addition to a test result to provide the physician (and the patient) with information how a test derived a particular test label. For example in the case of the Covid-19 test for a patient classified as lowest risk for ICU admission it would say (again, for example) that the first split was dominated by LDH and CRP, and the second split by ferritin, and the tree part by weight and gender. This might be useful for the physician to plan future treatment and triage.

VII Further Considerations

Even though the strategies for the evaluation of Shapley values using Monte-Carlo sampling of subsets outlined above do not require retraining of the classifier, they still require substantial compute resources. The required time for generating Shapley vales per sample, per 1M Monte-Carlo subsamples, and per 1,000 dois varies from ~6 hours (~50 features) to ~25 hours (~270 features) on a modern CPU using a single thread.

A priori it is not clear how many Monte-Carlo subsamples are necessary for a given sample to achieve a required level of accuracy allowing for a meaningful interpretation of the resulting Shapley values. In practice, this decision is made by the available compute resources. A post-hoc analysis studying convergence by sample is necessary.

Exact calculations dealing with missing features at the doi level using the method of 3.1 require full subset sampling, and CPU time grows exponentially as a function of feature number M. The CPU time requirement for the calculations dealing with missing features at the mini-classifier level is controlled by the number of mini-classifiers per doi, L, the number of features per mini-classifier, and the number of dois. In a use case of more features than development set samples, typical for a molecular diagnostic test, the number of features used within each doi, $nf_{doi}$, will be limited by the number of samples used in training rather than the total number of features used within the test, M, while the number of dois required to minimally sample the mini-classifiers will be polynomial in M. Taking a specific example, using pairs of features in the mini-classifiers and L=10, $nf_{doi} \leq 20$, and we have a reduction in the number of terms in the subset sums for the approach of 3.2 relative to the approach of 3.1 by a factor of $2^{M-nf_{doi}}$, yielding a polynomial scaling of CPU time with M. Hence, it is feasible to calculate the summations exactly, without resorting to Monte-Carlo subset sampling. The hierarchical approach of section 5.2 reduces the number of necessary terms by a further factor of $2^{nf_{doi}-L}$ (about 1000 in typical tests designed with this architecture). We have confirmed that the elapsed CPU time per doi, training/internal validation set split, mini-classifier, and sample is a constant independent of the total number of features used in the test when exact Shapley values are calculated using the hierarchical approach of section 5.2.

In view of the above, the computer system 10 shown in FIG. 1 could take the form of a single general purpose computer or a combination of computers, a set of computing processors arranged in parallel, or any other configuration of computing resources designed for the task of implementing classification models and calculating SVs in accordance with the teachings herein.

The ideas developed here should be applicable to other ML models with similar structure. For example, in deep learning networks, one could calculate the SVs for a specific node in the network, with "players" being the input nodes of the previous layers, and use a decomposition formula to evaluate the SVs of this node with players now being the input variables of the previous layer nodes. However, this requires a full SV calculation summing over all subsets of inputs for a node. Hence, one will only get a meaningful reduction in computational load if one restricts the connectivity of the nodes between layers to a tractable number (in the order of 10s). In practical implementation, this could be achieved with standard software tools like Tensorflow (http://tensorflow.org) by inserting suitably designed dropout layers. Work is in progress to create a library using these ideas.

In our real-world example, we already observed nontrivial structure of SV patterns that might be related to differing biology giving rise to the same prognostic outcome group. Having the ability to sub-divide sample cohorts into these subsets, possibly exhibiting different underlying biology, should be very helpful in translational studies attempting to elucidate the biological causes of disease progression. More detailed information might be derived by using SVs to study variable importance measures (see Williamson and Feng, *Efficient nonparametric statistical inference on population feature importance using shapley values*. Proceedings of Machine Learning Research, 119, 2020), and fast, reliable and computationally efficient SV calculation is important for the feasibility of such studies. SVs calculated for the real-world data in the setting of molecular diagnostics can be used to explain what features were most important in deriving the test prediction for an individual patient. They can be provided to physicians to facilitate physician/patient discussion of test results, for example using the reports shown in FIGS. 9-11 or the equivalent.

While presently preferred embodiments have been described with particularity, it will be appreciated that all questions concerning the scope of the invention are to be determined by reference to the appended claims.

We claim:

1. A method executing within a programmed computer to predict a patient outcome with a trained machine learning classifier, comprising the steps of:

(a) training the trained machine learning classifier arranged as a logistical combination of atomic classifiers with drop-out regularization, wherein the drop-out regularization comprises randomly selecting a small fraction of the atomic classifiers as a result of carrying out a dropout from the set of atomic classifiers;

(b) storing a set of values for attributes associated with a patient to the programmed computer to access an electronic health record of the patient or from one or more measurements obtained from the patient or sample obtained therefrom, or both;

(c) executing the trained machine learning model to classify the set of values with the trained machine learning classifier and generate the prediction using the programmed computer to classify the set of values with the trained machine learning classifier;

(d) calculating a relative contribution of some or all of the attributes to the prediction to generate an explanation of the prediction using the programmed computer; wherein calculating the relative contribution comprises either calculating exactly or estimating Shapley values for the attributes and wherein calculating the relative contribution comprises selecting subsets of the attributes to calculate the Shapley values by drawing a number of attributes associated with the patient for a subset and then randomly picking the attributes used within the subset, for dropout iterations; and (e) displaying a report using the programmed computer, wherein the report comprises (1) the prediction of risk of future adverse event for the patient while hospitalized, (2) data representing the calculation of the relative contribution of some or all of the attributes from step (d), either in text or graphical format, and wherein the report is for planning or adjusting a treatment for the patient.

2. The method of claim 1, wherein step (b) comprises performing a physical measurement on the sample obtained from the patient, and wherein the report comprises one or more of a first comment on the prediction and a second comment on the data.

3. The method of claim 1, wherein step (b) comprises performing a physical measurement comprising mass spectrometry.

4. The method of claim 2, wherein the physical measurement comprises a genomic or proteomic assay.

5. The method of claim 1, wherein the patient comprises a hospitalized patient and wherein the attributes comprise clinical and demographic data and findings obtained at admission to a hospital and wherein the prediction comprises a prediction of risk of future adverse event for the patient while hospitalized.

6. The method of claim 1, wherein the trained machine learning classifier comprises a hierarchical arrangement of a binary classifier and one or more child classifiers, wherein the method further comprises the step of calculating the Shapley values for one or more of the attributes for predictions generated by both the binary classifier and the one or more child classifiers, and wherein the atomic classifiers of the trained machine learning classifier are k-nearest neighbor classifiers.

7. The method of claim 1, wherein the Shapley values for the one or more of the attributes are calculated by a Monte Carlo sampling method, and wherein step (e) comprises presenting the Shapley values using one or more radar plots around a comment corresponding to the prediction and one or more of the Shapley values.

8. The method of claim 1, wherein the Shapley values for the one or more of the attributes are calculated as averages for multiple drop-out iterations.

9. The method of claim 6, wherein calculating the relative contribution of step (d) is performed in accordance with one of:

using subset sampling using least squares, evaluating pairwise differences of the Shapley values, and decomposing the Shapley values for drop-out iterations.

10. The method of claim 5, further comprising the step of using the report generated in step (e) to plan or adjust a treatment for the patient.

11. The method of claim 1, further comprising the step of using the report generated in step (e) to plan or adjust a treatment for the patient.

12. The method of claim 8, wherein calculating the relative contribution is performed by calculating one of the Shapley values as an average for multiple drop-out iterations.

13. The method of claim 7, wherein the Shapley values are calculated as a solution of a linear system.

\*    \*    \*    \*    \*